United States Patent [19]
Watari et al.

[11] Patent Number: 5,585,271
[45] Date of Patent: Dec. 17, 1996

[54] YEAST AGGLUTINATION GENES AND YEAST CONTAINING THEM

[75] Inventors: Junji Watari; Yoshihiro Takata; Masahiro Ogawa, all of Yaizu, Japan; Merja Penttila, Espoo, Finland; Maija-Leena Onnela, Espoo, Finland; Sirkka Keranen, Espoo, Finland

[73] Assignees: Sapporo Breweries Ltd., Tokyo, Japan; Oy Panimolaboratorio-Bryggerilaboratorium AB, Espoo, Finland

[21] Appl. No.: 325,267
[22] PCT Filed: Feb. 24, 1994
[86] PCT No.: PCT/JP94/00290
§ 371 Date: Nov. 18, 1994
§ 102(e) Date: Nov. 18, 1994
[87] PCT Pub. No.: WO94/19475
PCT Pub. Date: Sep. 1, 1994

[30] Foreign Application Priority Data

Feb. 26, 1993 [JP] Japan .................... 5-038871

[51] Int. Cl.$^6$ .............. C12N 15/31; C12N 15/81; C12N 1/19
[52] U.S. Cl. ............ 435/254.2; 536/23.1; 536/23.2; 536/23.74; 435/69.1; 435/71.1; 435/172.3; 435/254.11; 435/254.21; 435/255.1; 435/255.2; 435/261
[58] Field of Search ............... 536/23.1, 23.2, 536/23.74; 435/69.1, 71.1, 172.3, 254.11, 255.1, 254.2, 254.21, 255.2, 261

[56] References Cited

FOREIGN PATENT DOCUMENTS

WO04/01567  1/1994  WIPO.
WO94/18330  8/1994  WIPO.

OTHER PUBLICATIONS

J. Warari et al. "Breeding of Flocculent Brewer's Yeast by Genetic Engineering", Proc. Congr. Eur. Brewery Convention, 23rd, 297–304 (1991).

A. W. Teunissen et al. "Northern Studies of the *FL01* Gene of *Saccharomyces cerevisiae*", Yeast 8, Spec. Iss. S621 (1992).

Yeast, vol. 9, No. 4, Apr. 1993, A. W. R. H. Teunissen, et al., "Sequence of the Open Reading Frame of the FL01 Gene from *Saccharomyces cerevisiae*", pp. 423–427.

Agric. Biol. Chem., vol. 55, No. 6, 1991, pp. 1547–1552, Junji Watari, et al., "Breeding of Flocculent Industrial *Saccharomyces cerevisiae* Strains by Introducing the Flocculation Gene FL01".

Agricultural and Biological Chemistry, vol. 53, No. 3, Jan. 1989, Junji Watari, et al., "Molecular Cloning of a Flocculation Gene in *Saccharomyces cerevisiae*", pp. 901–903.

Yeast, vol. 9, No. 1, Jan. 1993, Aloys W. R. H. Teunissen, et al., "Physical Localization of the Flocculation Gene FL01 on Chromosome I of *Saccharomyces cerevisiae*", pp. 1–10.

*Primary Examiner*—Robert A. Wax
*Assistant Examiner*—Rebecca Prouty
*Attorney, Agent, or Firm*—Oblon, Spivak, McClelland, Maier & Neustadt, P.C.

[57] ABSTRACT

An agglutination gene of 4.7±0.2 kb in yeast which codes for a polypeptide which exhibits agglutinative activity.

3 Claims, 11 Drawing Sheets

YEAST AGGLUTINATION GENES AND YEAST CONTAINING THEM

TECHNICAL FIELD

The present invention relates to agglutination genes of agglutinative yeast, and to yeast which contains them.

BACKGROUND ART

In the fermentation industry, yeast agglutination is an industrially important phenomenon, and the use of agglutinative yeast is being studied while much research is being undertaken to discover the cause of its agglutination. Yeast agglutination is known to be controlled by a plurality of genes, a relatively well researched example thereof being the agglutination gene called FL01, which is mapped on the right arm of yeast chromosome I.

Regarding the structure of the agglutination gene FL01 derived from the yeast *Saccharomyces cerevisiae*, it had been completely unknown, but in 1989 it was cloned for the first time by the present inventors et al., and its restriction enzyme cleavage map has been determined (Watari et al., Agricultural and Biological Chemistry, Vol. 53, No. 3, p.901–903, 1989). (Nevertheless, it base sequence was unknown).

We the present inventors reported that it is possible to convert non-agglutinative industrial yeasts into agglutinative yeasts for practical use by the introduction of the agglutination gene FL01 into various industrial yeasts (Watari et al., Agricultural and Biological Chemistry, Vol. 55, No. 6, p.1547–1552, 1991); however, it was not always possible to impart strong and stable agglutinative properties to all of the industrial yeasts.

We the present inventors thereafter diligently pursued research on the FL01 gene, and discovered that the gene that we the present inventors et al. had reported as being the FL01 gene (Watari et al., Agricultural and Biological Chemistry, Vol. 53, No. 3, p. 901–903, 1989) was not the intact FL01 gene as present on chromosome I of the yeast *Saccharomyces cerevisiae* strain ABXL-1D, but was the FL01 gene with a portion thereof deleted during maintenance of the plasmid containing the intact FL01 gene in *Escherichia coli* strain K12 (hereunder, this gene shall be referred to as FL01S).

DISCLOSURE OF INVENTION

The object of the present invention is to establish the structure of the intact FL01 gene (hereunder, this gene shall be referred to as FL01L), and to provide a technique for imparting stronger and more stable agglutinative properties to various industrial yeasts.

Now, we the present inventors, as the result of varied research regarding the FL01 gene, have succeeded in isolating the intact FL01 gene, or FL01L gene, have determined the entire base sequence of the gene, and further have discovered that by using the FL01L gene, it is possible to breed various yeasts for practical use which have stronger and more stable agglutinative ability, compared with using the FL01S gene, and thus the present invention has been completed.

In other words, the present invention relates to an agglutination gene of 4.7±0.2 kb in yeast which codes for a polypeptide which exhibits agglutinative activity, and specifically, it relates to the above mentioned agglutination gene which is derived from the yeast *Saccharomyces cerevisiae* and is defined by the restriction enzyme cleavage map in FIG. 1, and more specifically, it relates to the above mentioned agglutination gene which substantially codes for the amino acid sequence listed as Sequence No. 1 (SEQ ID No: 1).

The present invention also relates to an agglutination gene of 2.6±0.2 kb in yeast which codes for a polypeptide which exhibits agglutinative activity, and specifically to an agglutination gene which is derived from the yeast *Saccharomyces cerevisiae* and is defined by the restriction enzyme cleavage map in FIG. 2, and more specifically, to an agglutination gene which substantially codes for the amino acid sequence listed as Sequence No. 3 (SEQ ID No: 3).

The present invention further relates to yeasts containing either of the above mentioned agglutination genes and having agglutinative properties.

"Agglutination gene" as mentioned in the present specification is used to mean a gene which controls agglutination of yeast.

Effect of the Invention

As described above, the agglutination genes according to the present invention are capable of imparting agglutinative properties to the non-agglutinative yeast *Saccharomyces cerevisiae*. Here, the significance of using agglutinative yeasts in the fermentation industry is that 1) the cells may be rapidly separated from the fermented mash after completion of fermentation, and thus the process may be simplified so that there is no need for other procedures for the separation of the yeast from the fermented mash involving use of a centrifugal separator, etc.; 2) the clarity of the fermented mash is high, and thus the burden is reduced during the final filtration of the fermented mash, and productivity is increased; 3) continuous fermentation is possible in the same manner as with immobilized cells, and no reactors or other special equipment are necessary. Furthermore, breeding of agglutinative yeast has been attempted in the past using an induction method, cross-breeding method, cell fusion method, etc. for natural or artificial mutants, but it is often reported that these methods are necessarily accompanied by a change in the genetic properties of the original strain to be bred, also usually destroying the desirable properties of the original strain. However, according to the present invention, it is possible to improve the agglutinative properties of the strain to be grown simply by introduction thereinto of the genes according to the present invention, and the fact that they do not damage the other desirable properties of the original strain is their major advantage.

In the figure, the cleavage sites of each of the restriction enzymes are represented by Ac for AccI, Bg for BglII, RV for EcoRV, K for KpnI and Pv for PvuII.

Figure 1:
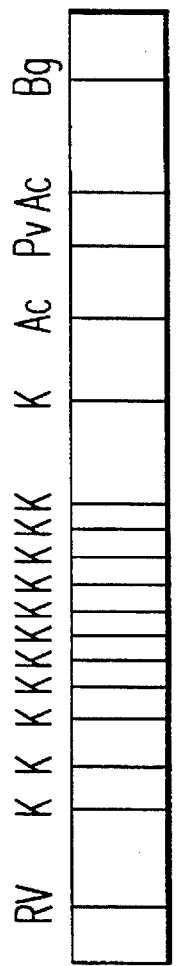
FIG. 1 A restriction enzyme cleavage map of the FL01L gene according to the present invention.
Figure 2:
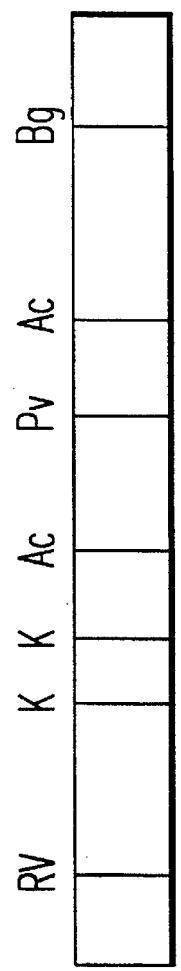

FIG. 2 A restriction enzyme cleavage map of the FL01S gene according to the present invention. In the figure, the cleavage sites of each of the restriction enzymes are represented by Ac for AccI, Bg for BglII, RV for EcoRV, K for KpnI and Pv for PvuII.

Figure 3:
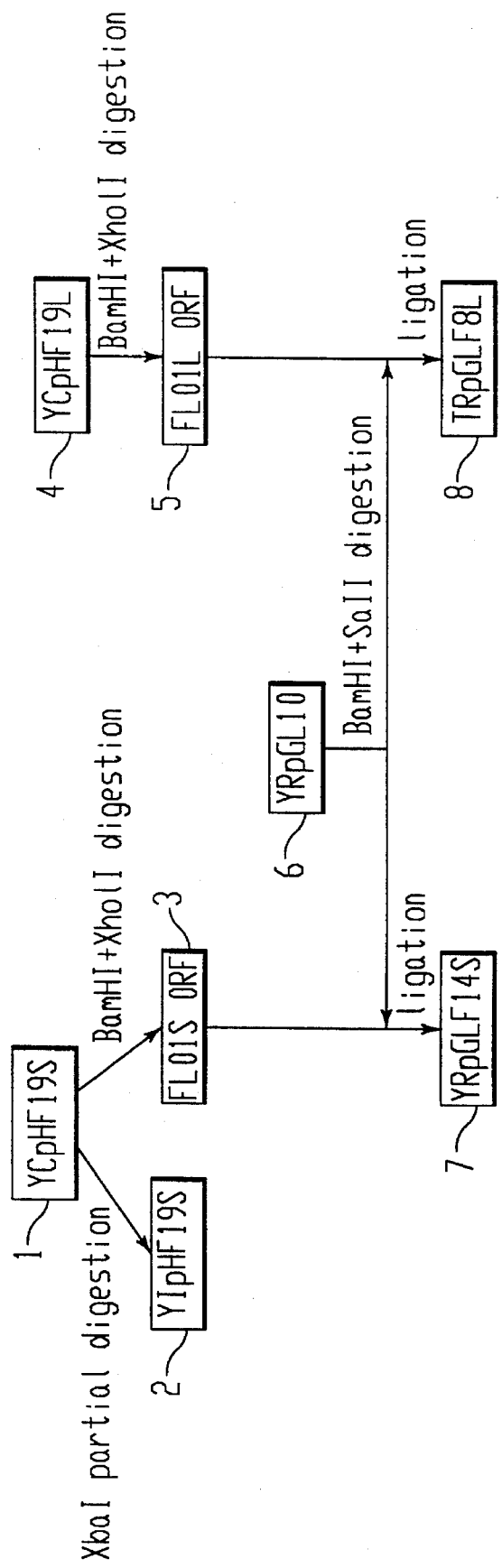

FIG. 3 A flow chart for the preparation of plasmids YRpGLF14S and YRpGLF8L containing the agglutination genes FL01S and FL01L, for direct selection of the yeasts.

Figure 4:
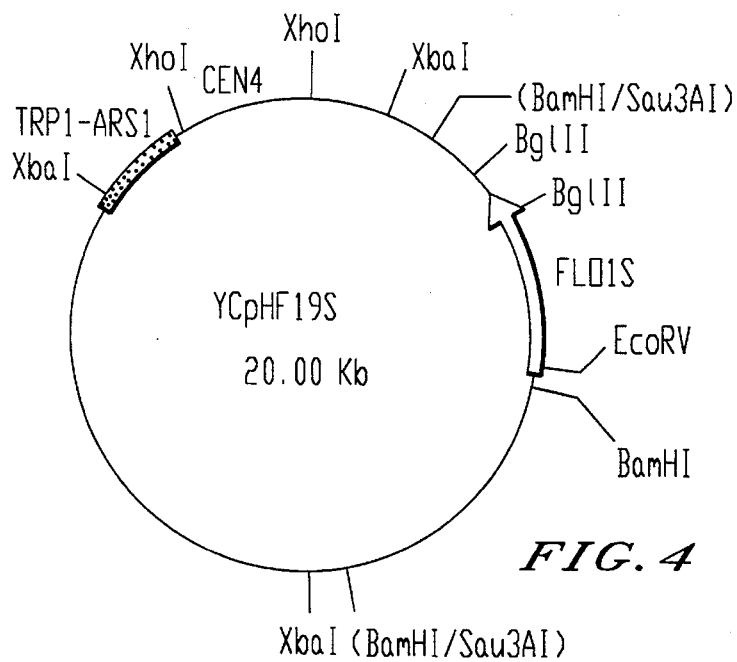

FIG. 4 YCpHF19S (20.00 Kb).

Figure 5:
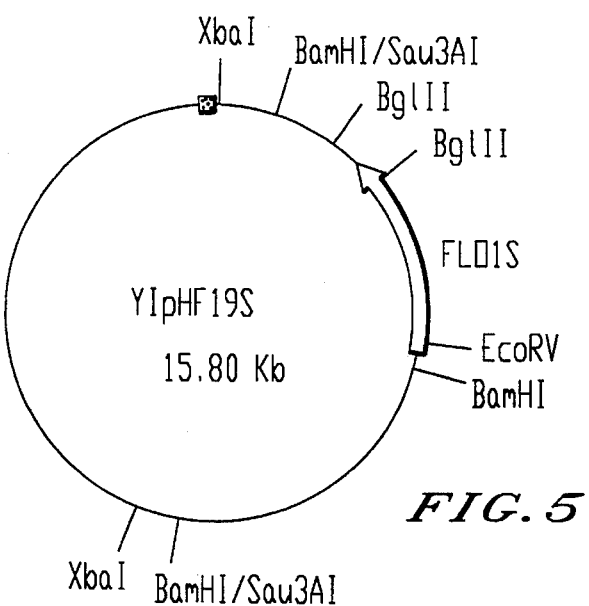

FIG. 5 YIpHF19S (15.80 Kb).

Figure 6:
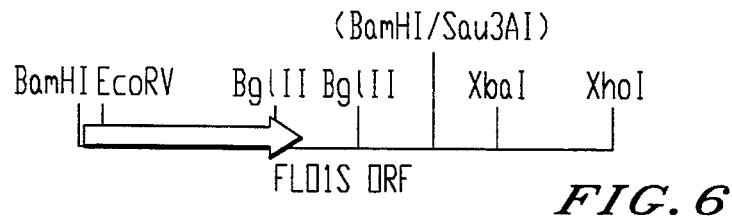

FIG. 6 5.8 kb BamHI-XhoI fragment of YCpHF19S containing the FL01S gene.

Figure 7:
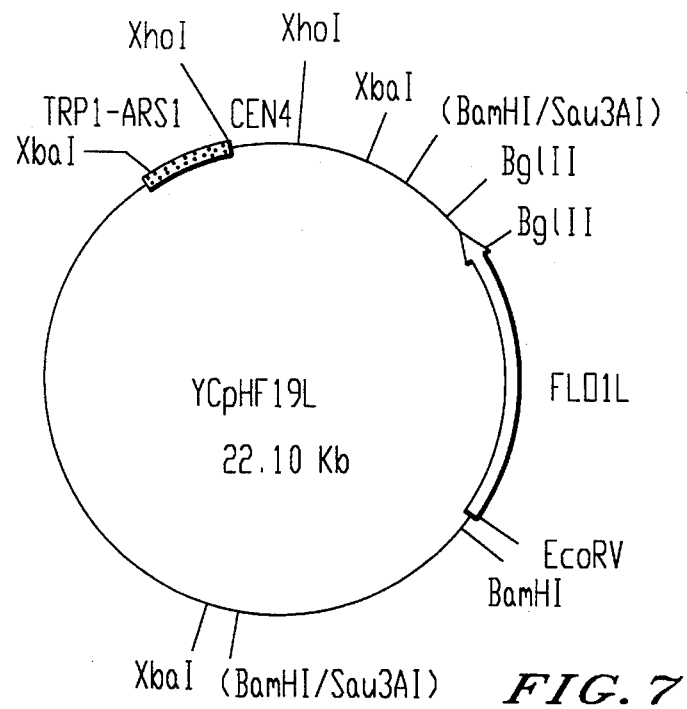

FIG. 7 YCpHF19L (22.10 Kb).

Figure 8:
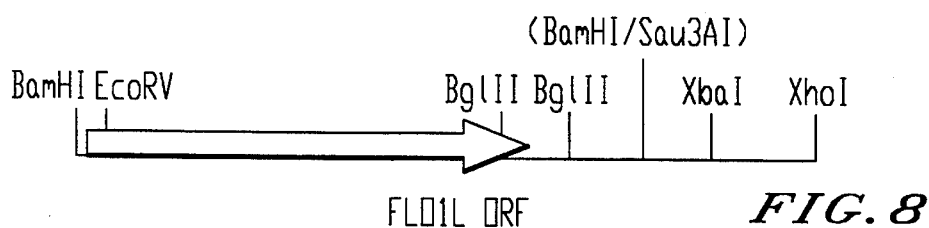

FIG. 8 7.9 kb BamHI-XhoI fragment of YCpHF19L containing the FL01L gene.

Figure 9:
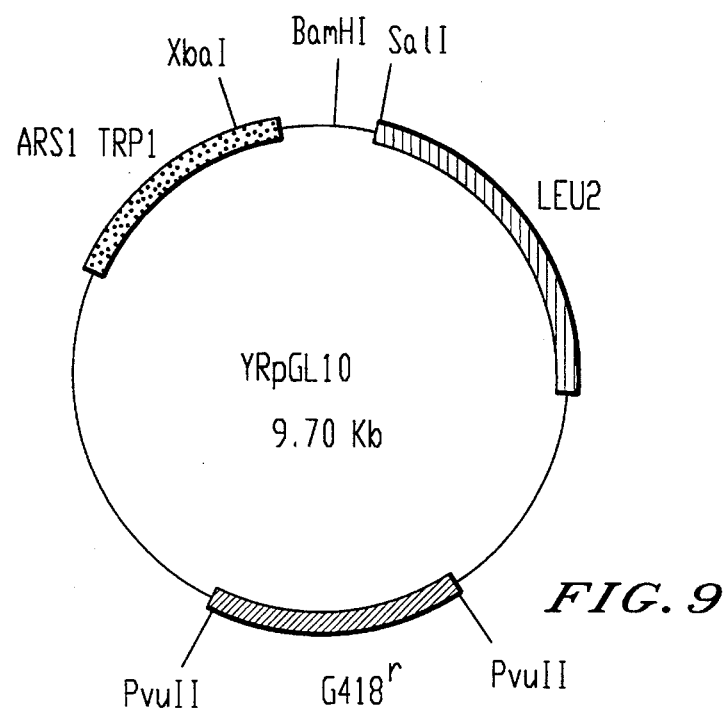

FIG. 9 YRpGL10 (9.70 Kb).

Figure 10:
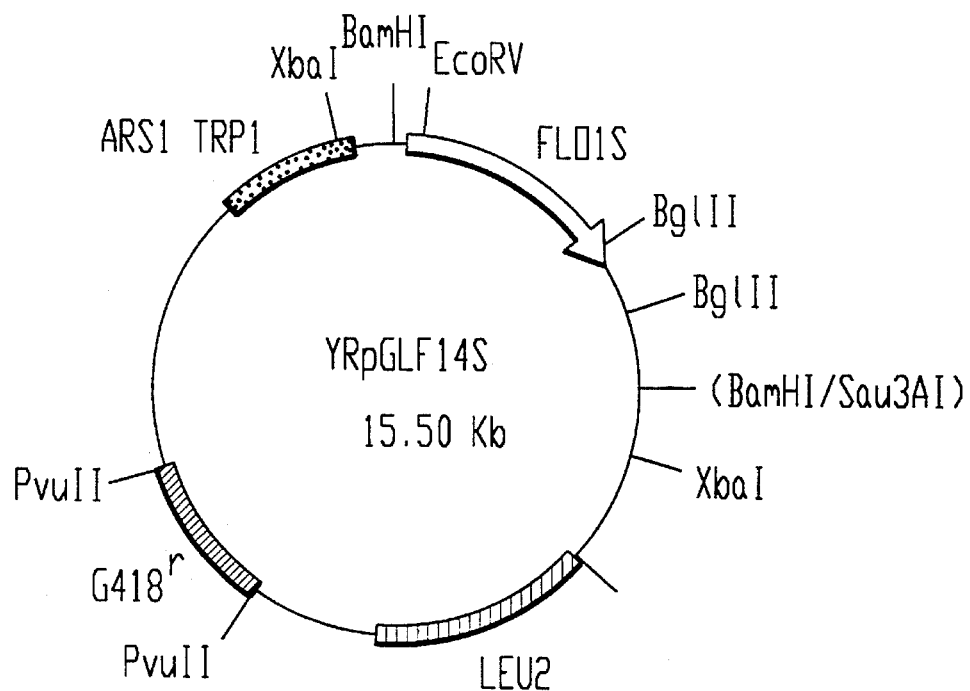

FIG. 10 YRpGLF14S (15.50 Kb).

Figure 11:
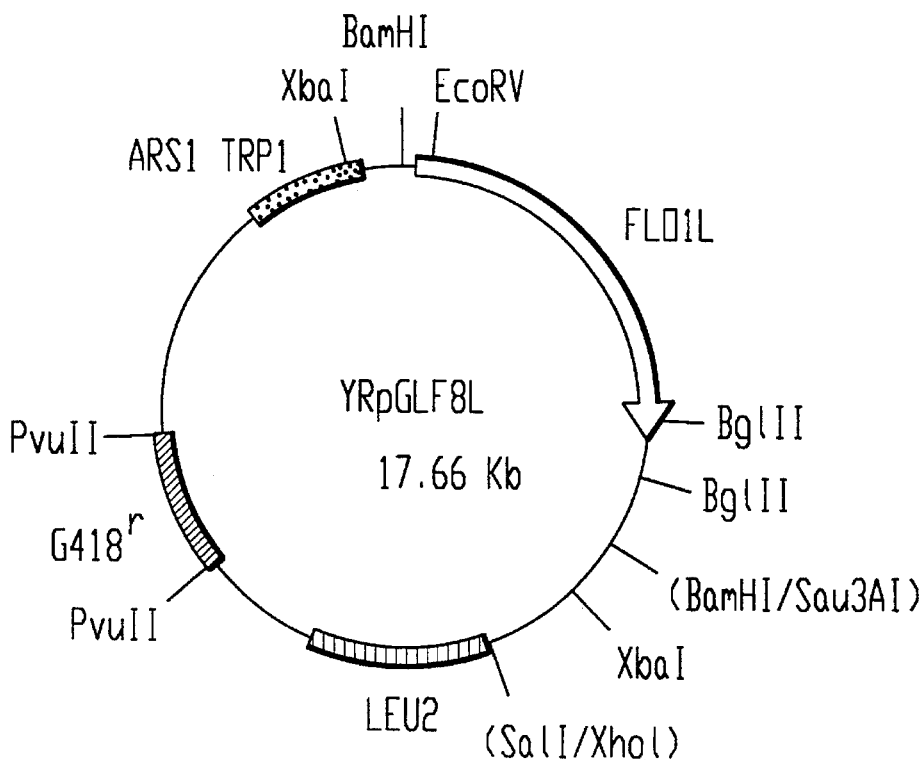

FIG. 11 YRpGLF8L (17.66 Kb).

Figure 12:
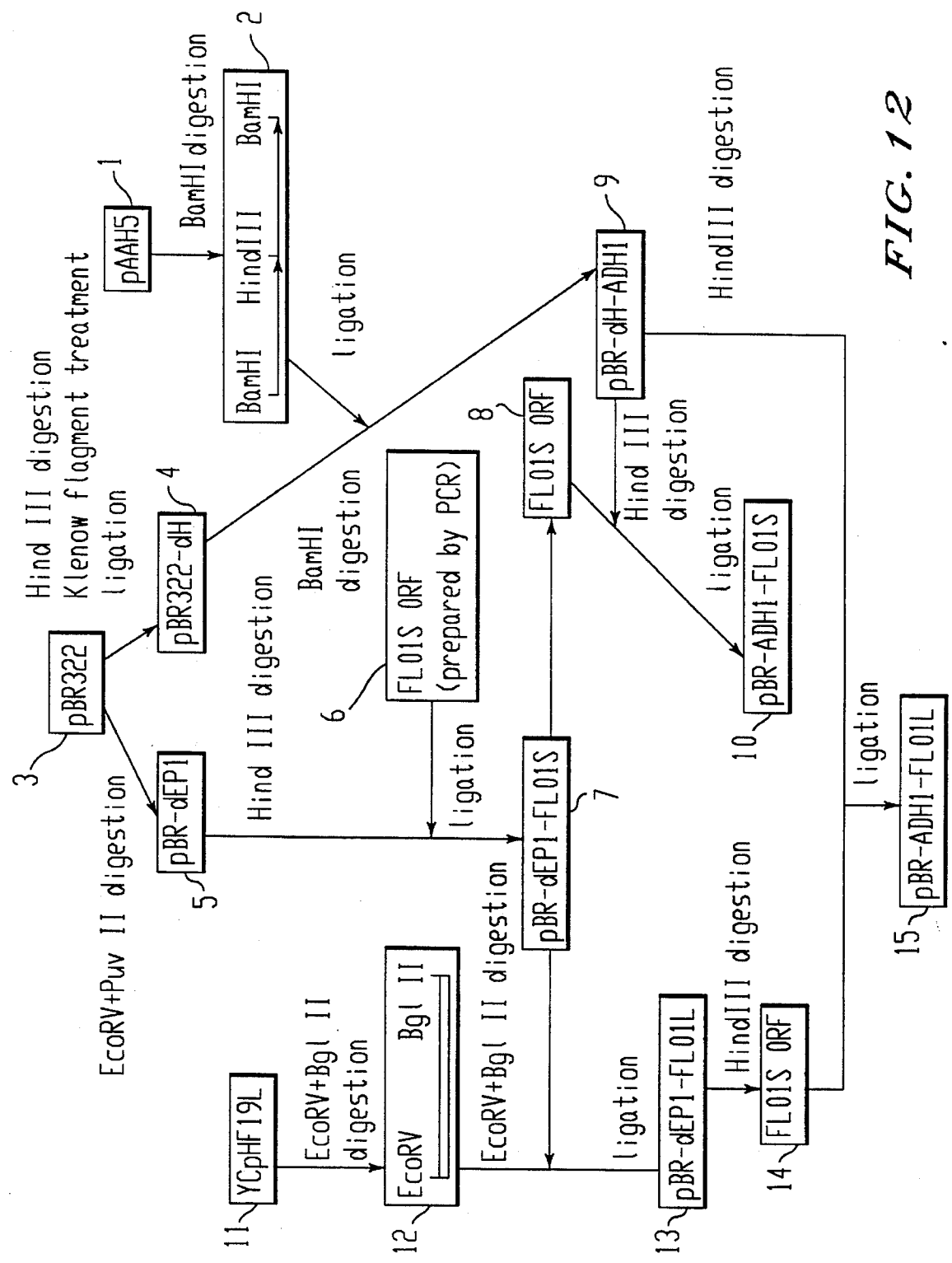

FIG. 12 A flow chart for the preparation of plasmids pBR-ADH1-FL01S and pBR-ADH1-FL01L containing the agglutination genes FL01S and FL01L, for incorporation onto the yeast chromosomes.

Figure 13:
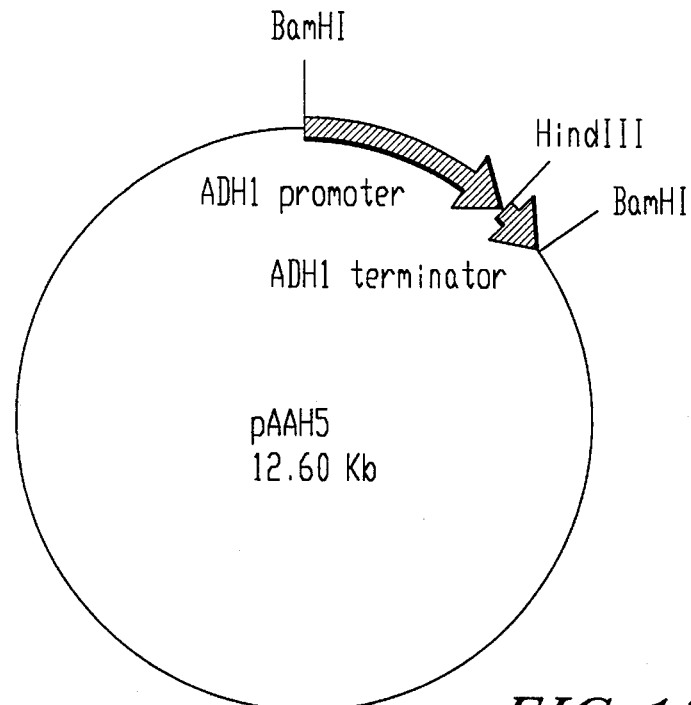

FIG. 13 pAAH5 (12.60 Kb).

Figure 14:
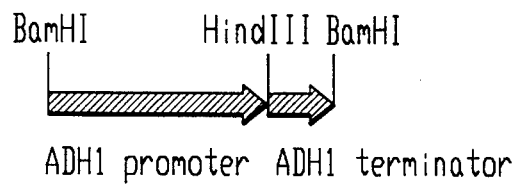

FIG. 14 BamHI-digested pAAH5 (12.60 Kb).

Figure 15:
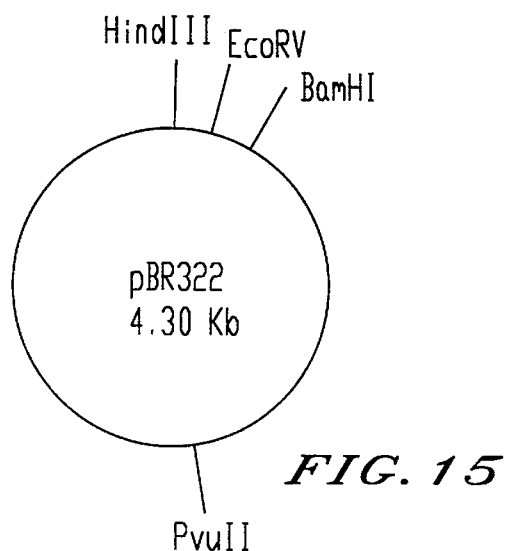

FIG. 15 pBR322 (4.30 Kb).

Figure 16:
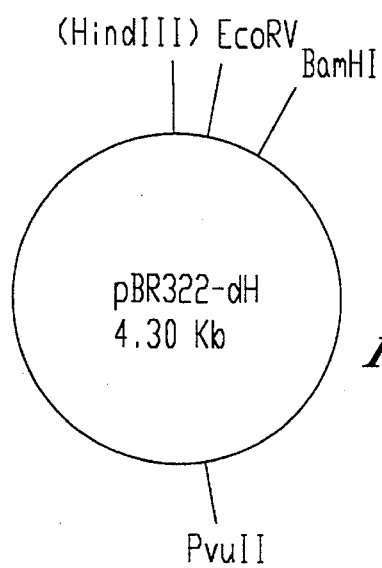

FIG. 16 pBR322-dH (4.30 Kb).

Figure 17:
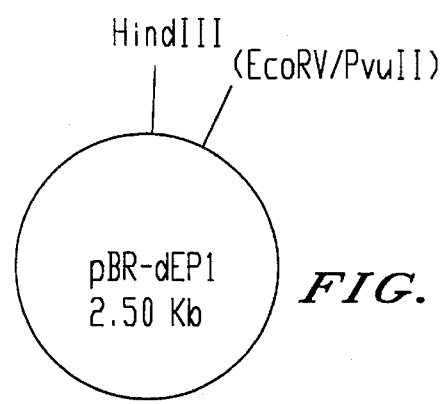

FIG. 17 pBR-dEP1 (2.50 Kb).

Figure 18:
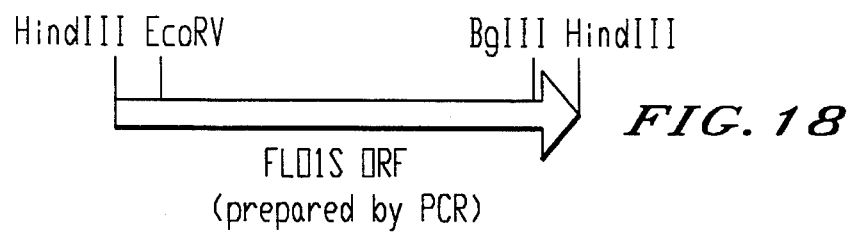

FIG. 18 The open reading frame of FL01S prepared by PCR.

Figure 19:
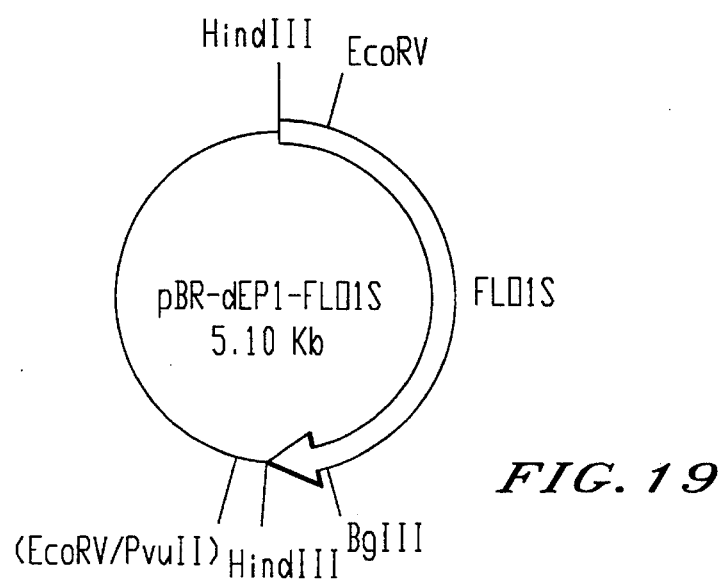

FIG. 19 pBR-dEP1-FL01S (5.10 Kb).

Figure 20:
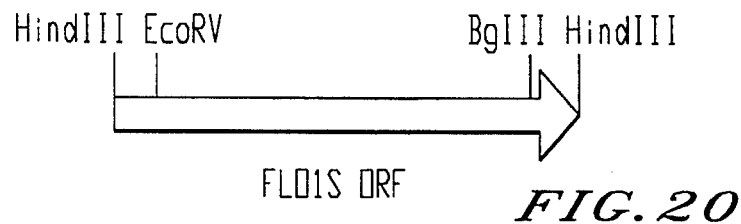

FIG. 20 The open reading frame of FL01S.

Figure 21:
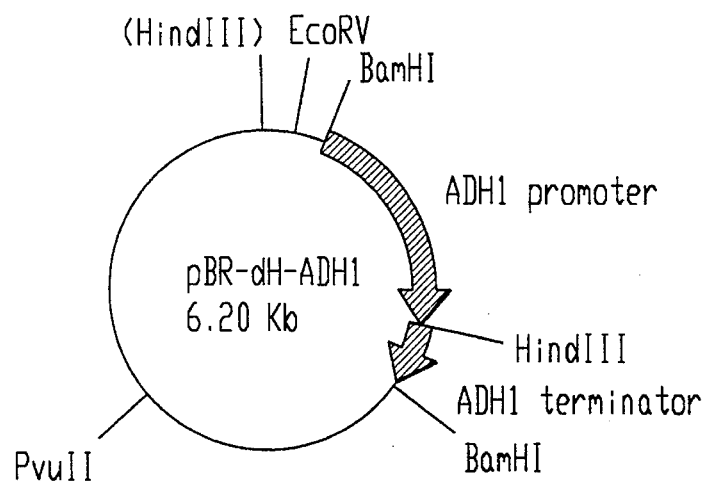

FIG. 21 pBR-dH-ADH1 (6.20 Kb).

Figure 22:
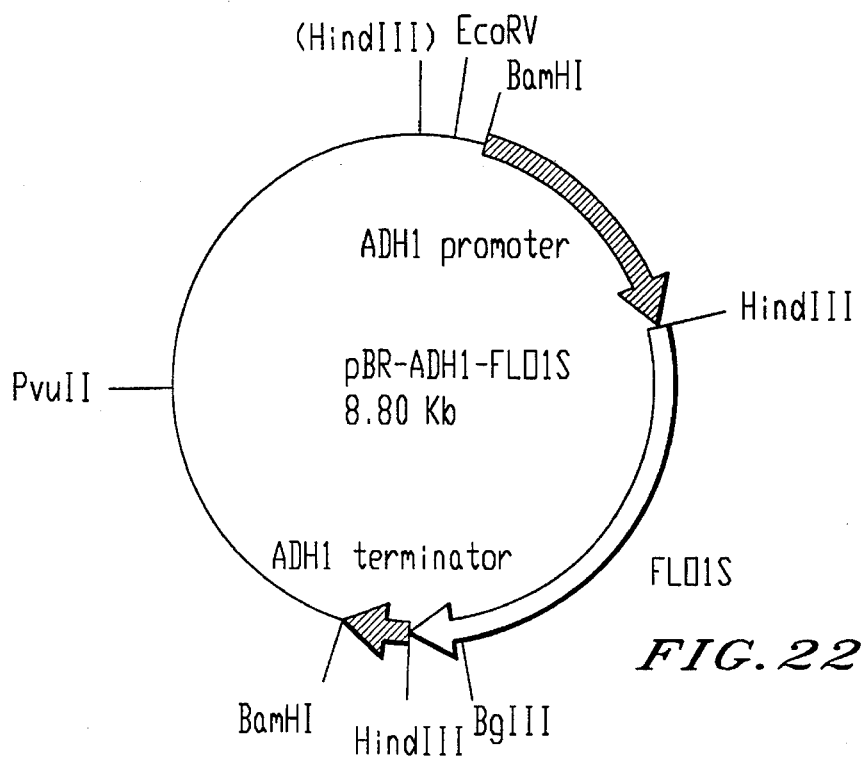

FIG. 22 pBR-ADH1-FL01S (8.80 Kb).

Figure 23:
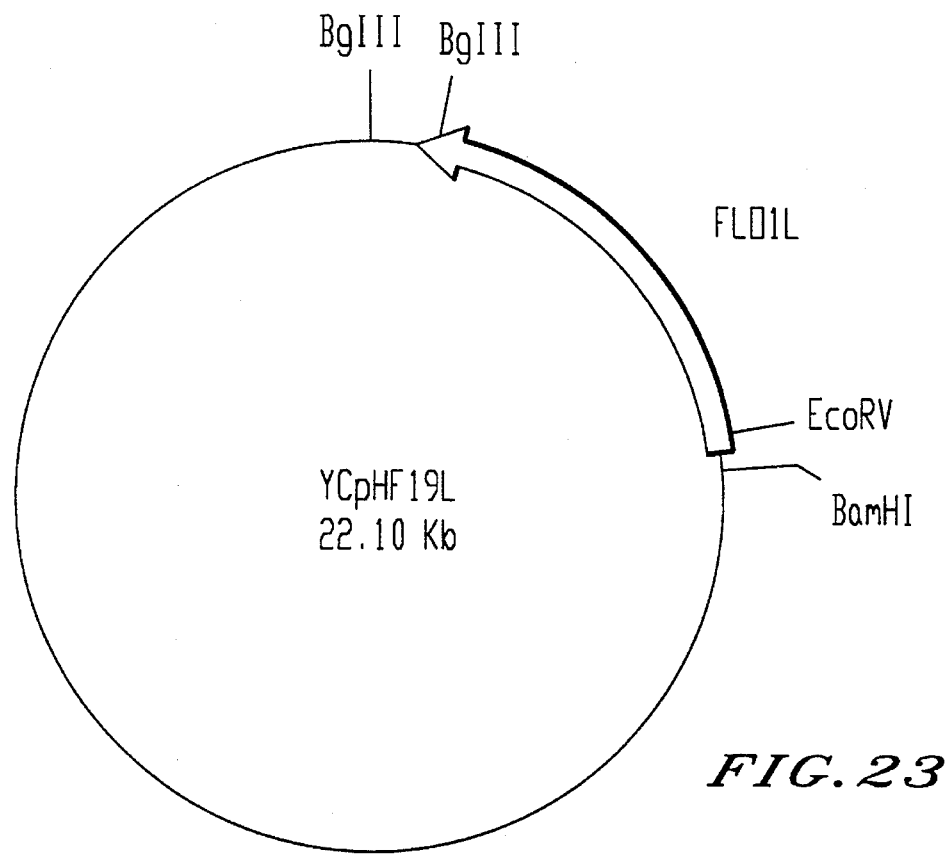

FIG. 23 YCpHF19L (22.10 Kb).

Figure 24:

FIG. 24 EcoRV+BglII-digested YCpHF19L.

Figure 25:
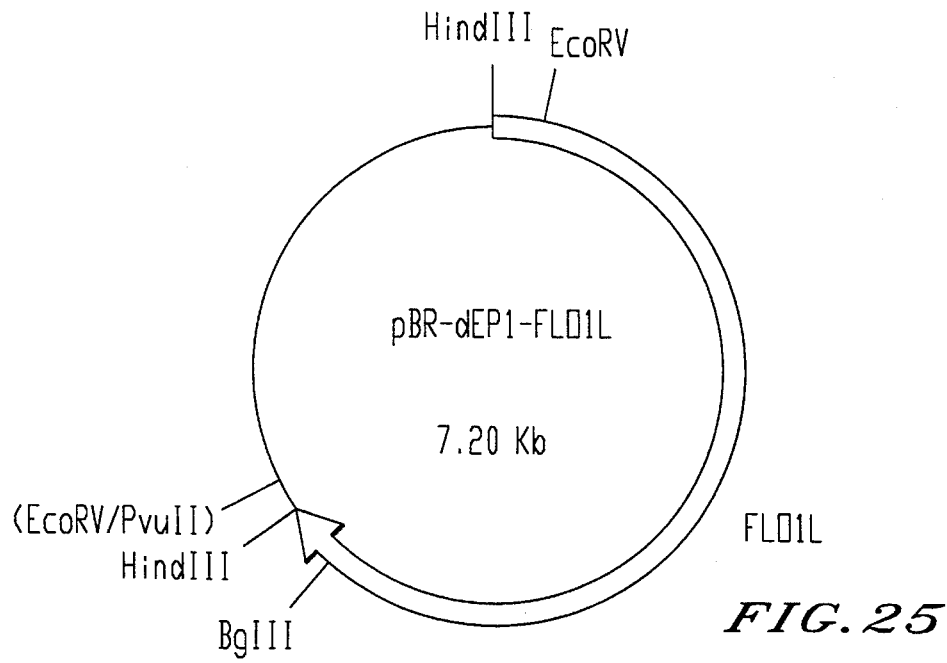

FIG. 25 pBR-dEP1-FL01L (7.20 Kb).

Figure 26:
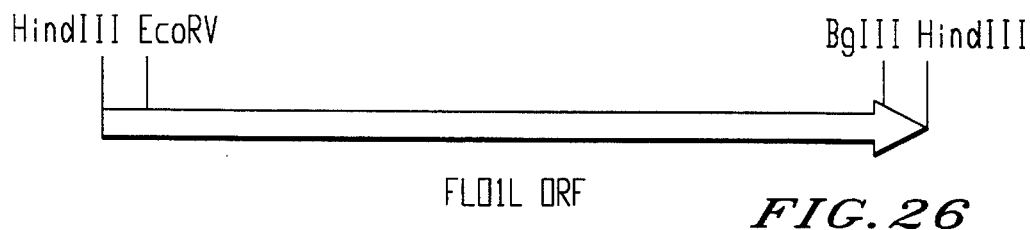

FIG. 26 The open reading frame of FL01L.

Figure 27:
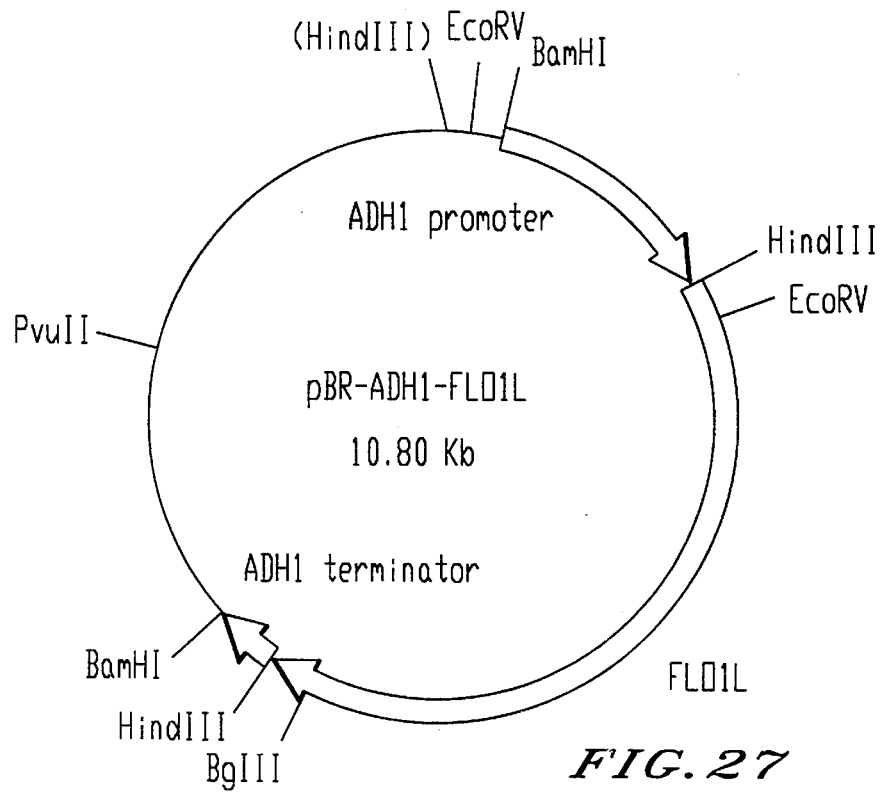

FIG. 27 pBR-ADH1-FL01L (10.80 Kb).

BEST MODE FOR CARRYING OUT THE INVENTION

A more concrete explanation of the present invention is provided below.

Agglutination gene

The genes according to the present invention which impart agglutinative properties to the yeast *Saccharomyces cerevisiae* include a gene of 4.7±0.2 kb in yeast which codes for a polypeptide which exhibits agglutinative activity and an agglutination gene of 2.6±0.2 kb derived from the above mentioned agglutination gene, and these genes correspond respectively to the FL01L gene (also abbreviated to FL01L) and the FL01S gene (also abbreviated to FL01S) derived from the agglutination gene FL01 of the yeast *Saccharomyces cerevisiae* described above. FL01S is the FL01L gene with a portion of the base sequence deleted. In addition, as described later, the FL01 gene also encompasses genes which are artificial or naturally occurring derivatives of the FL01L gene and have agglutinative activity, although the lengths of their open reading frames may differ. Here, the FL01L gene is the intact FL01 gene on chromosome I of the yeast *Saccharomyces cerevisiae*, and FL01S is the F101L gene with a portion of the open reading frame deleted in-frame. Here, characteristically FL01L imparts a relatively strong agglutinative property to the host yeast into which it is introduced, while FL01S imparts a weaker agglutinative property to the host yeast in comparison to FL01L.

The agglutination genes according to the present invention are present in the yeast *Saccharomyces cerevisiae* in the form of plasmids which contain the genes as their constituents, and in the form of insertions into the genome of the host. Also, for a stable expression of the agglutination genes in the yeasts, the agglutination genes according to the present invention may be placed under the control of an appropriate promotor and terminator, and be present in this form as plasmids or as insertions into the genome. The promotor and terminator used may be suitable combinations of publicly known ones, such as alcohol dehydrogenase gene (ADH1), phosphoglycerate kinase gene (PGK), etc.

Polypeptides coded for by genes

The FL01L gene according to the present invention is specified by the amino acid sequence of the polypeptide for which it codes. This polypeptide has agglutinative activity and it is one whose amino acid sequence is substantially represented by Sequence No. 1 (SEQ ID No: 1). Here, the expression "one whose amino acid sequence is substantially represented by Sequence No. 1 (SEQ ID No: 1)" means that some of the amino acids may be deleted or substituted, or some amino acids may be added thereto, so long as the polypeptide has agglutinative activity.

A typical polypeptide according to the present invention which exhibits agglutinative activity is one which has the amino acid sequence listed as Sequence No. 1 and consists of 1,537 amino acids, and its amino acid sequence has not been known in the past.

It was stated above that, according to the present invention, the expression "one whose amino acid sequence is substantially represented by Sequence No. 1 (SEQ ID No: 1)" means that some of the amino acids may be deleted or substituted, or some amino acids may be added thereto, so long as the polypeptide has agglutinative activity; an example of a peptide which has such an alteration relating to its amino acids is one in which the 329th to the 1,003rd amino acids of the amino acid sequence listed as Sequence No. 1 (FL01L sequence) are deleted (FL01S sequence, see Sequence No. 2 (SEQ ID No: 3), and this peptide has agglutinative activity, although somewhat weaker. If the agglutinative property of a yeast during fermentation is too strong, then the number of suspended yeast cells will be lowered and this will generally tend to slow the rate of fermentation, and it is therefore desirable to breed yeast in such a way that agglutinative properties of the proper strength are imparted in each of the fermentation systems. The agglutinative properties may become too strong with introduction of the FL01L gene, and thus introduction of the FL01S gene is sometimes preferable. In that sense, although the lengths of the polypeptides according to the present invention are basically that of the sequence listed as Sequence No. 1 (SEQ ID No: 1), the deletion, substitution, addition, etc. of a few amino acids is highly significant for establishing agglutination activities of desired strengths in various yeasts. That is, such altered polypeptides are within the scope of the polypeptides according to the present invention which have agglutinative activity.

Base sequence of agglutination gene

The DNA chain of the FL01L gene is one having the base sequence listed as Sequence No. 1 (SEQ ID No: 1) of the sequence list, or a degenerate isomer thereof, and having the base sequence which corresponds to the amino acid sequence listed as Sequence No. 1 (SEQ ID No: 1), or a degenerate isomer thereof. Here, "degenerate isomer" means a DNA chain which differs only in a degenerate codon, and is still capable of coding for the same polypeptide.

The base sequence of the DNA chain listed as Sequence No. 1 was determined for the FL01 gene obtained from *Saccharomyces cerevisiae* strain ABXL-1D (Yeast Genetic Stock Center, University of California, USA) using the dideoxy method.

Collection of DNA chain of agglutination gene

At present there is absolutely no information available regarding the product of the FL01 gene which has agglutinative activity (the amino acid sequence of the polypeptide coded for by the FL01 gene), and therefore it is impossible to clone the FL01 gene by the commonly employed hybridization method using an appropriate DNA probe which is chemically synthesized based on the amino acid sequence. As a result, we the present inventors constructed a gene library of the entire DNA of *Saccharomyces cerevisiae* strain ABXL-1D using a yeast/*E. coli* shuttle vector plasmid, and this non-agglutinative yeast was transformed therewith to obtain an agglutinative clone, and plasmids were recovered from the transformed strain (see following Examples for details).

Introduction of agglutination gene into yeast

By introduction of the DNA chain of the agglutination gene according to the present invention which was obtained in the manner described above into yeasts which are used in the fermentation industry, for example, brewer's yeast, wine yeast, whiskey yeast, Japanese sake yeast, shochu yeast, alcohol production yeast, etc. (all of *Saccharomyces cerevisiae*) according to bioengineering methods, it is possible to convert them into agglutinative strains if they are non-agglutinative strains, or reinforce their agglutinative properties if they are agglutinative strains.

Yeasts

The yeasts to be transformed according to the present invention are yeasts belonging to the genus *Saccharomyces cerevisiae* described in *The Yeasts: A Taxonomic Study*, 3rd Ed. (Yarrow, D., ed. by N. J. W. Kreger-Van Rij. Blsevier Science Publishers B. V., Amsterdam, 1984, p.379), or their synonyms or mutants; however, in light of the object of the present invention, the various industrial yeasts belonging to the genus *Saccharomyces cerevisiae*, for example, brewer's yeast, wine yeast, whiskey yeast, Japanese sake yeast, shochu yeast, alcohol production yeast, etc. are preferred.

Specific examples thereof include bottom brewer's yeast: W164 (Munich Institute of Technology, Germany), W204 (Munich Institute of Technology, Germany), SMA-S (Berlin Institute of Technology), H. H. (Berlin Institute of Technology), top brewer's yeast: obg. 160 (Berlin Institute of Technology, Germany), wine yeast: IAM 4175 (Tokyo University), whiskey yeast: AHU3200 (Hokkaido University), Japanese sake yeast: Association No. 6 (Japan Brewing Association), shochu yeast: IFO 0282 (Fermentation Research Institute Foundation), alcohol production yeast: IFO 0216 (property of Fermentation Research Institute), etc. These industrial yeasts have been selected and pure cultured over a period of many years into forms suitable for the fermentation industry, that is, forms which are capable of efficiently fermenting fermentation sources, which produce alcohol with a good flavor, and whose genetic properties are stable, etc.

Transformation

The procedures and methods of preparing the transformant may be those commonly used in the fields of molecular biology and genetic engineering, and they may include methods other than those mentioned below according to the present invention as long as they are effected using common techniques. In order to express the agglutination gene according to the present invention in yeast, it is necessary to first insert the gene into a plasmid vector which exists stably in the yeast. The plasmid vector used here may be any of the known ones, such as YRp, YEp, YCp, YIp, etc. These plasmid vectors are not only publicly known by document, but they are also easy to prepare.

The marker to be used for selection of the desired transformant according to the present invention may be a resistance gene against a drug such as G418, etc., since there are no particularly appropriate intrinsic genetic markers requiring amino acids or nucleic acids, etc. in the case of industrial yeasts. However, using the fact that the present agglutination gene is expressed as the dominant gene, it is possible to obtain a transformant which is marked with the agglutination itself.

The insertion of the DNA chain of the agglutination gene according to the present invention into the plasmid and introduction thereof into the yeast is easily effected, but on the other hand, this type of plasmid usually cannot be stably maintained in the cells, and often escapes from the transformed cells.

In order to maintain the DNA chain of the agglutination gene according to the present invention in the yeast in a more stable manner, it may be inserted into the genome of the yeast. Particularly in the case of yeasts used in the food industry, it is more preferable to improve the yeast only with the yeast genes, without having a non-yeast DNA fragment from *E. coli* (contained in the plasmid vector if the plasmid was grown up in *E. coli*) present in the final recombinant. Here, we the present inventors chose to introduce only the yeast gene, using the co-transformation method of Penttila, et al. and the gene replacement method (Current Genetics, Vol. 12, p.413–420, 1987) by which only the yeast gene is incorporated into the genomic DNA. Also, the transformation here may be effected by any appropriate desired method which is commonly used in the fields of molecular biology or genetic engineering, such as, for example, the protoplast method of Hinnen, et al. (Proceedings of National Academy of Sciences of the United States of America, Vol. 75, p.1929–1933, 1978), the lithium acetate method of Itoh, et al. (Journal of Bacteriology, Vol. 153, p.163–168, 1983), etc. The yeast according to the present invention obtained in this manner has, except for the introduced exogenous DNA, exactly the same genetic properties as the original strain before introduction, and further, by using the chromosome introduction method wherein only the DNA chain of the agglutination gene according to the present invention is introduced by the above mentioned co-transformation and gene replacement methods, no unnecessary vector sequences are contained therein, and thus the obtained recombinant yeast has none of the properties of the vector which is used. As a result, the superior character of the original strain is in no way impaired, and it is possible to breed industrial yeasts whose agglutination is improved in a specific manner.

Production of alcoholic liquors

Fermentation of the fermentation source using a yeast transformed by an agglutination gene according to the present invention such as the one mentioned above, may be carried out to achieve the effects described above. As is obvious, the fermentation source is to be chosen depending on the object of fermentation; for example, wort is used in the production of beer and whiskey, fruit juice in the production of wine, koji in the production of Japanese sake, starch or carbohydrate sources in the production of shochu, and molasses, starch or carbohydrate sources in the production of alcohol. In addition, the conditions of fermentation may be the same conditions as conventionally used, and there is no need to modify the existing fermentation procedures or equipment when applied to the present invention.

Since the yeast which is used exhibits agglutination in the alcoholic liquor produced thereby, it rapidly agglutinates and settles at the bottom of the fermentation vat after completion of the fermentation, and the yeast cells are readily separable from the fermentation mash.

EXAMPLES

A more detailed description of the present invention is provided below with reference to the Examples.

Example 1 (Collection of gene controlling agglutination of yeast)

The following experiment was conducted to obtain the FL01S gene as one of the agglutination genes according to the present invention (Watari, et al., Agricultural and Biological Chemistry, Vol. 53, No. 3, p.901–903, 1989). The chromosomal DNA of Saccharomyces cerevisiae strain ABXL-1D (gene type: MATa FL01, Yeast Genetic Stock Center, University of California, USA) was prepared according to the method of Cryer, et al. (Methods of Cell Biology, Vol. 12, p.39–44, 1975). The obtained chromosomal DNA was partially digested with the restriction enzyme Sau3AI, DNA fragments of over 5 kb were recovered by sucrose density gradient centrifugation, and the DNA fragments were inserted in vitro by a ligation reaction at the BamHI region of the cloning vector YCpH4 (Watari, et al., Agricultural and Biological Chemistry, Vol. 53, No. 3, p.901–903, 1989) which contained the histidine synthesis gene HIS4 as a selection marker. *Escherichia coli* (*E. coli*) strain MC1061 (gene type: hsdR mcrB araD139^(araABC-leu)7679^lacX74 galU glaK rpsL thi) was transformed with the ligation mixture, and the plasmids were extracted from the transformant to prepare a gene library for strain ABXL-1D. *E. coli* strain MC1061 is a strain in wide use in the field of recombinant DNA technology.

Using this gene library, the histidine-requiring non-agglutinative baker's yeast *Saccharomyces cerevisiae* strain YJW6 (gene type: MAT–ade1ural his4 can1 kar1) (Agricultural and Biological Chemistry, Vol. 53, No. 3, p.901–903, 1989) was transformed. The transformation of *Saccharomyces cerevisiae* strain YJW6 was effected basically according to the lithium acetate method of Itoh, et al. (Journal of Bacteriology, Vol. 153, p.163–168, 1983). That is, to 100 ml of a YPD liquid culture medium (1% yeast extract, 2% bactopeptone, 2% glucose) was inoculated one loopful of YJW6 strain and the cells were cultured at 30° C. overnight, separated with a centrifuge the following morning, inoculated into a new medium of the same composition and further cultured for 3 hours at 30° C. The collected cells were washed with 40 ml of sterilized water, and then finally suspended in 20 ml of a TE solution (10 mM Tris-HCl buffer solution containing 1 mM of EDTA, pH 7.5). Of this, 5 ml was transferred to an L-shaped test tube (Monod tube), 5 ml of a 0.2M lithium acetate solution was added thereto, and the mixture was shaken at room temperature for 1 hour, at 100 cycles/min. From the mixture 0.1 ml was taken and added to a 1.5 ml Eppendorf tube which already contained 50 µg of the recombinant plasmid (ethanol precipitated, and then air-dried), and the mixture was stirred well and allowed to stand for 30 minutes at 30° C. The Eppendorf tube was then stirred well, 0.1 ml of 70% polyethylene glycol #4,000 was added thereto, and the mixture was further stirred well and then allowed to stand for 1 hour at 30° C. This was heated at 42° C. for 5 minutes (heat shock treatment), allowed to cool to room temperature, and then the cells were washed with sterilized water. Finally, the cells were suspended in 0.5 ml of sterilized water, and the solution was applied 0.1 ml at a time to a minimal culture medium which contained no histidine (0.67% Difco yeast nitrogen base without amino acids, 2% glucose, 40 µg/ml adenine sulfate, 40 µg/ml uracil, 2% Difco bacto agar), to obtain a non-histidine-requiring transformant. This transformation experiment was repeated 10 times to obtain approximately 10,000 clones of the non-histidine-requiring transformant.

Next, the agglutinative clones were screened out of the transformants. The transformants were taken from the plate one at a time using a toothpick, inoculated into a 96-well microplate [each well containing 200 µl of a minimal liquid culture medium (above mentioned minimal medium with agar removed)], and cultured at 25° for 3 days. The agglutination was examined by vigorously shaking the microplate after culturing, using a microplate mixer (Titech micromixer) for 60 seconds, and visually locating the agglutinative clones. One clone of relatively strong aggglutinative properties was obtained out of approximately 6,000 non-histidine-requiring transformants. This strain was cultured in a non-selective YPD culture medium, upon which a clone which had become histidine-requiring, that is, which had lost the plasmid, was obtained. This clone, in becoming histidine-requiring, had also lost its agglutinative properties. In addition, when DNA was recovered from the originally obtained agglutinative transformants, the plasmid was recovered from *E.coli* strain MC1061, and non-histidine-requiring transformants were obtained by retransforming strain YJW6 therewith, all were agglutinative. These results led to the conclusion that the agglutination exhibited by the transformed strain was not due to any genetic mutation in the host cell, but was caused by the plasmid in the transformed strain. Here, we the present inventors named the plasmid which contained the genetic sequence controlling agglutination, YCpHF19S. The restriction enzyme map thereof is shown in FIG. 4.

As may be surmised from the screening test for the agglutinative yeast using the microplate, such a plasmid which contains the agglutination gene may be used as a marker for the selection of agglutination from yeast which do not have a marker, in order to obtain the transformants. In this experiment as well, transformants in which the present plasmid had been introduced were actually obtained from the non-agglutinative yeast. In other words, this type of agglutination gene may clearly be used for obtaining transformants of yeast belonging to *Saccharomyces cerevisiae* without any genetic marker. Furthermore, during the screening process, there are merits in having basically no need to prepare a special culture medium (minimal medium or medium containing antibiotics) for screening for the transformants, and in culturing in a normal culture medium. Also, there are presently few yeast-derived genetic markers for obtaining yeast transformants, and they are very useful in yeast self-cloning experiments.

Example 2

(Mapping and identification of cloned agglutination gene)

In order to determine whether or not the agglutination gene cloned in Example 1 was the FL01 gene on yeast chromosome I, the following physical mapping experiment was conducted with the present agglutination gene (Watari, et al., Agricultural and Biological Chemistry, Vol. 53, No. 3, p.901–903, 1989).

An EcoRV fragment of 2.6 kb taken from the region of DNA in the plasmid YCpHF19S which contained the gene controlling agglutination, was used as a probe, and physical mapping of the present gene fragment on the chromosome was effected by chromosome DNA electrophoresis (pulse field electrophoresis). That is, chromosome electrophoresis of *Saccharomyces cerevisiae* strain ABXL-1D was effected by using the method of Carle, et al. (Proceedings of the National Academy of Sciences of the United States of America, Vol. 82, p.3756–3760, 1985) to prepare a sample, and using a Biorad CHEF electrophoresis apparatus. After completion of the electrophoresis, the DNA band on the electrophoresis gel was subjected to Southern blotting and hybridization, following the method of Maniatis, et al. (Molecular Cloning, p.382–389, Cold Spring Harbor Laboratory, 1982). As a result, the above mentioned 2.6 kb EcoRV fragment hybridized to chromosome I of strain ABXL-1D, indicating that the agglutination gene cloned in the present experiment was the gene on chromosome I.

Next, genealogical mapping of the cloned agglutination gene was attempted (Watari, et al., Agricultural and Biological Chemistry, Vol. 55, No. 6, p.1547–1552, 1991). YCpHF19S was partially digested with the restriction enzyme XbaI, and the yeast centromere gene (CEN4) and the yeast replication origin ARS1 were removed to prepare the YIp plasmid YIpHF19S (see FIG. 5) to be incorporated. After this plasmid was digested with the restriction enzyme BamHI to raise the efficiency of incorporation of the cloned agglutination gene portion into the yeast, *Saccharomyces cerevisiae* strain YJW2A (gene type: MATa FL01 his4) was transformed therewith by the method described above to obtain a non-histidine-requiring transformant. The obtained strain was crossed with *Saccharomyces cerevisiae* strain YJW6 (gene type: MAT–ade1 ura1 his4 can1 kar1) to obtain a diploid, which was sporulated and subjected to genetic analysis (tetrad analysis). As a result, genealogical linkage (parental ditype:nonparental ditype:tetratype=22:0:7) was accomplished between the His+ characteristic (non-histidine-requiring) and ADE1 on chromosome I, clearly showing that the cloned agglutination gene portion of the YIpHF19S plasmid had been incorporated on chromosome I of strain YJW2A.

From the above results of physical and genealogical mapping, we the present inventors concluded that the cloned agglutination gene was the FL01 gene on yeast chromosome I. However, at this point, it was not known that the FL01 gene obtained here was not the intact FL01 gene as present on the yeast chromosome (or, the FL01L gene), but rather the FL01S gene lacking a portion of the DNA sequence of FL01L, as described below.

Example 3

(Analysis of base sequence of FL01S)

We the present inventors conducted an experiment to determine the base sequence of the FL01 gene (actually the FL01S gene) obtained above.

AS a result of subcloning, it had been discovered that the region necessary for the expression of agglutination by the FL01S gene consisted of the 4.1 kb DNA fragment between BamHI-(BamHI/Sau3AI) of the plasmid YCpHF19S. Here, the region containing this DNA fragment was subcloned at the multi-linker sites of the sequencing vectors pUC118 and puC119 (both products of Takara Brewing Co.). Next, each of the subclones were subjected to the method of Henikoff, et al. (Gene, Vol. 28, p.351–359, 1984) and the method of Yanisch-Perron, et al. (Gene, Vol. 33, p.103,119, 1985), by treating the insertion sections of their plasmids with exonuclease III and mangbean nuclease, resulting in the preparation of short lengths on various clones with the inserted fragment partially missing and thus differing chain lengths. During this process, a kilosequencing deletion kit (product of Takara Brewing Co.) was used. Regarding the inserted fragments of the resulting various clones, the dideoxy method of Sanger, et al. (Science, Vol. 214, p.1205–1210, 1981) was followed and an automatic DNA sequencer of Applied Biosystems Japan, Inc. was used to determine the base sequence of the above mentioned 4.1 kb DNA fragment. As a result of the analysis thereof, an open reading frame of 2,586 bp (SEQ ID No: 3) was found to be present which is capable of coding for a polypeptide of 862 amino acids with an estimated molecular weight of 89,368.

Example 4

(Southern hybridization experiment)

As described above, the agglutination gene obtained in Example 1 was clearly at the FL01 locus on yeast chromosome I, but in order to determine whether or not this was the intact FL01 gene, a Southern hybridization experiment such as the following was conducted. First, all of the DNA was extracted from the yeast *Saccharomyces cerevisiae* strain ABXL-1D from which the agglutination gene had been cloned, and was completely digested with restriction enzyme EcoRV and subjected to electrophoresis, and then to genomic Southern analysis using as a probe the 2.6 kb EcoRV DNA fragment containing the open reading frame mentioned above in Example 2. Here, the Southern blotting and hybridization were effected according to the method of Maniatis, et al. (Molecular Cloning, p.382–389, Cold Spring Harbor Laboratory, 1982).

The results were that, surprisingly, no hybridization signal was detected at the location corresponding to approximately 2.6 kb, but a hybridization signal was obtained at the location corresponding to approximately 4.7 kb. This led the present inventors to suppose that the cloned agglutination gene might not be identical to the FL01 gene of strain ABXL-1D, but rather might be the intact FL01 gene with a portion of the DNA sequence lost for some reason during the cloning process.

Example 5

(PCR (polymerase chain reaction) experiment)

Here, the present inventors conducted an experiment such as the following to confirm the structure of the FL01 gene of ABXL-1D, by the PCR (polymerase chain reaction) method. First, a DNA chain was chemically synthesized using the base sequence mentioned above in Example 3. That is, a DNA sequence of 33 bases including the initiation codon region of the open reading frame of the present gene was chemically synthesized with a DNA synthesizer (product of ABI Co.) and used as the PCR 5' probe.

(Sequence No. 3)

5'-CCC<u>AAGCTT</u>AAAAATGACAATGCCTCATCGCTA-3'

HindIII
    Linker site (The ATG– starting at the 14 th base from the 5' end of the above sequence is the 5' end sequence of FL01S).

In addition, a DNA sequence of 33 bases was chemically synthesized in the same manner, which included a complementary strand (reverse strand) of the region containing the termination codon of the open reading frame of the present agglutination gene, and this was used as the PCR 3' probe (SEQ ID No: 6).

(Sequence No. 4)

5'-CCC<u>AAGCTT</u>TTAAATAATTGCCAGCAATAAGGA-3'

HindIII
Linker site (The TTA– starting at the 10 th base from the 5' end of the above sequence is the 3' end sequence of FL01S (reverse strand)).

Next, using these 5' and 3' probes, the PCR experiment was conducted with the entire DNA of *Saccharomyces cerevisiae* strain ABXL-1D as the template.

A zymoreactor Model AB-1800 (product of Ato Co.) was used for the PCR experiment, and Pfu DNA polymerase (Stratagene Co.) was used as the DNA polymerase. Also, the conditions of the PCR experiment were according to the method of Inis, et al. (PCR Technology, p.3–12, Stockton Press, ed. Henry A. Erlich, 1989). Upon confirmation of the bands of the DNA amplified as a result of the PCR experiment by electrophoresis on an agarose gel, a single band was obtained in the area of approximately 4.7 kb, and it was surmised that the open reading frame of FL01 of strain ABXL-1D was approximately 4.7 kb. Further, in a control experiment in which plasmid YCpHF19 containing the agglutination gene cloned by the present inventors was used as the template, a band in the area of approximately 2.6 kb was obtained. From these results, the present inventors concluded that the intact open reading frame of FL01 gene as present in the yeast *Saccharomyces cerevisiae* strain ABXL-1D is approximately 4.7 kb, and not approximately 2.6 kb.

Therefore, we the present inventors concluded that the agglutination gene obtained by us was the FL01 gene with a portion thereof missing for some reason, most likely as a result of intramolecular recombination during the process of maintaining YCpHF19 in *E. coli* strain MC1061.

Example 6

(Collection of FL01L gene)

Here, we the present inventors made a reexamination based on our expectation that the plasmid containing the intact FL01 gene might be contaminated in the YCpHF19S plasmid solution initially recovered from *E. coli*, during the cloning of FL01. First, a portion of the plasmid solution was taken, digested with the restriction enzyme EcoRV and subjected to electrophoresis on an agarose gel, upon which an extremely faint but clearly observable band was discovered in the area of 4.7 kb, in addition to the 2.6 kb band obtained for YCpHF19S. This suggests that the plasmid solution is a mixture of two types of plasmids. Here, we the present inventors used this plasmid solution to transform *E. coli* strain JA221 (gene type: recA1, lacy leuB trp^E5 thr thi hsdR hsdM), and upon extraction of the plasmids from the obtained transformants and examination thereof, another type of plasmid was separated in addition to YCpHF19S, which was approximately 2.1 kb larger than YCpHF19S. Here, initially cloned plasmid was named YCpHF19S, and the plasmid separated from the YCpHF19S plasmid solution which was 2.1 kb longer was named YCpHF19L. Also, as a result of analysis of the respective restriction enzyme cleavage patterns of YCpHF19S and YCpHF19L, the plasmids were found to have no differences in any DNA regions other than the DNA region containing the open reading frame of the agglutination gene (see FIGS. 4 and 7). That is, the open reading frame of the agglutination gene of YCpHF19L was shown to be 2.1 kb longer than that of YCpHF19S. This led to the conclusion that the initial cloning of the intact FL01 gene (i.e., FL01L) was successful, but during the process of maintaining the YCpHF19L plasmid in *E. coli* strain MC1061, a portion of the open reading frame of the FL01L gene had been deleted in-frame, converting FL01L to FL01S, or YCpHF19L to YCpHF19S, due to intramolecular recombination in vivo. Here, it was thought that since the deletion occurred inframe, FL01S was still capable of coding for a polypeptide exhibiting agglutinative properties.

Distinction shall hereunder be made between FL01S as the agglutination gene on YCpHF19S, and FL01L as the agglutination gene on YCpHF19L.

Further, the frequency of occurrence of the deletion is greatly influenced by the type of *E. coli* maintaining the YCpHF19L plasmid, and the present inventors discovered the phenomenon that, for example, a high rate of conversion occurs with strain MC1061 (gene type: hsdR mcrB araD139^(araABC-leu)7679^lacX74 galU galK rpsL thi) and strain DH5–(gene type: supE44^lacU169(-801acZ^M15) hsdR17-recA1 endA1 gyrA96 thi-1relA1), whereas comparatively little conversion occurs with strain JA221 (gene type: recA1 lacy leuB trp^B5 thr thi hsdR hsdM). Therefore, the present inventors mainly used strain JA221 when the plasmid was maintained in *E. coli*. However, at present the reason for this conversion is not clear.

Example 7

(Analysis of base sequence of FL01L)

The DNA fragment containing FL01L was cut off from the YCpHF19L plasmid obtained above, and its entire base sequence was determined by exactly the same method as in Example 3. As a result, it was confirmed that the open reading frame of FL01L was a base sequence of 4,611 bp which codes for a polypeptide of 1,537 amino acids with an estimated molecular weight of 160,692 (Sequence No. 1). Also, it was shown that FL01S is FL01L with an inframe deletion of a DNA chain consisting of the 985th to the 3,009th bases from the initiation codon of the open reading frame (corresponding to the 329th to the 1,003rd amino acids of the amino acid sequence) (see SEQ. ID Nos. 1 and 3).

In addition, judging from the results of analysis of the amino acid sequence of FL01L, a repeated sequence (direct repeat) of 45 amino acids is found from the 278th to the 1,087th amino acids of the sequence [basically represented by the following sequence, with the amino acids separated by a "/" within the parentheses indicating alternative candidates. ThrThrThr(Glu/Gln)ProTrp(Asn/Thr/Asp)(Gly/Asp/Ser)ThrPheT hrSerThrSer(Thr/Ala)Glu(Met/Leu/Val)(Thr/Ser)Thr(Val/Ile) ThrGlyThrAsnGly(Leu/Val/Gln)(Pro/Arg)ThrAspGluThr(Val/Ile)IleVal(Ile/Vla)(Arg/Lys)ThrProThr(Thr/Ser)(Ala/Glu)(Thr/Gly/Ser/Ile)(Thr/Leu/Ser)(Als/Ile/Val/Ser)(Met/Ser/Ile/Thr) (SEQ. ID No: 7)], and in FL01L there are 18 of this repeated sequence. On the other hand, in FL01S, the major portion of the region of this repeated sequence is deleted (FL01S has the 329th to the 1,003rd amino acids of the amino acid sequence of FL01L deleted), and only 3 copies of the repeated sequence are present. The present inventors believe at the present time that the difference in the agglutinative capabilities of FL01L and FL01S (the former imparts a stronger agglutinative property to the host cell than does the latter), is connected with the number of these direct repeats. We the present inventors presume that in the future it will be possible to achieve a desired agglutinative capability for a cell, i.e. regulate agglutinative capabilities at will, by regulation of the number of direct repeats.

Example 8

[Introduction of FL01L gene into various yeast strains for practical use (1: using plasmid vectors)]

The agglutination genes FL01S and FL01L obtained above were introduced into various industrial yeasts (all non-agglutinative) to determine whether or not they are actually effective for the breeding of agglutinative yeast strains for practical use. First, plasmids were prepared which contained directly selectable FL01S or FL01L genes, for transformation of the industrial yeasts (A flow chart is shown in FIG. 3. The numbers next to each plasmid and open reading frame (ORF) in the flow chart match the numbers next to the plasmids and open reading frames shown in detail in FIGS. 4–11). A 5.8 kb BamHI-XhoI fragment (FIG. 6) containing the FL01S gene of YCpHF19S was inserted into the gap between BamHI-SalI of the plasmid YRpGL10 to be used for direct selection (having a G418-resistant Tn903 gene as the marker gene for direct selection, and an ARS1 sequence as the replication origin within the yeasts. See FIG. 9), to prepare the YRpGLF14S plasmid (FIG. 10). In addition, a 7.9 kb BamHI-XhoI fragment (FIG. 8) from YCpHF19L was inserted into the gap between BamHI-SalI of YRpGL10 to prepare YRpGLF8L as a similar plasmid containing the FL01L gene (FIG. 11).

The method used for transformation of the industrial yeasts by the plasmids will now be described. The method for transformation of the industrial yeasts was basically identical to the one used for the experimental yeasts described in Example 1, but the present inventors made some slight modifications as indicated below (Watari, et al., Agricultural and Biological Chemistry, Vol. 55, No. 6, p.1547–1552, 1991). That is, to 100 ml of a YPD liquid culture medium (1% yeast extract, 2% bactopeptone, 2% glucose) was inoculated one loopful of cells, which were cultured at 30° C. overnight, separated with a centrifuge the following morning, inoculated into a new medium of the same composition and further cultured for 3 hours at 30° C. The collected cells were washed with 40 ml of sterilized water, and then finally suspended in approximately 20 ml of a TE solution (10 mM Tris-HCl buffer solution containing 1 mM of EDTA, pH 7.5). (However, a hematometer was used here to adjust the concentration of the suspension to achieve a final cell concentration of about $2 \times 10^8$ cells/ml). Of this, 5 ml was transferred to an L-shaped test tube (Monod tube), 5 ml of a 0.2M lithium acetate solution was added thereto, and the mixture was shaken at room temperature for 1 hour, at 100 cycles/min. From the mixture, 0.1 ml was taken and added to a 1.5 ml Eppendorf tube which already contained 50 μg of the recombinant plasmid (ethanol precipitated, and then air-dried), and the mixture was stirred well and then allowed to stand for 30 minutes at 30° C. The Eppendorf tube was stirred well, 0.1 ml of 70% polyethylene glycol #4,000 was added thereto, and the mixture was stirred well and then allowed to stand for 1 hour at 30° C. Next, the mixture was heated to 42° C. for 5 minutes, (heat shock treatment), allowed to cool to room temperature, and then the cells were washed with sterilized water. Finally, the cells were suspended in 1.4 ml of a YPD solution in an Eppendorf tube, and cultured while standing for 16–20 hours at 30° C. The culture solution was then applied 0.1 ml at a time to a YPD agar medium containing 200 μg/ml of G418, and incubated at 30° C. for 2–3 days to obtain the transformants.

The experiment for transformation of various industrial yeasts was carried out using this method. The results are shown in Table 1. In addition, the method of evaluating the agglutination was as follows. Each of the transformants was inoculated into an L-shaped test tube (Monod tube) which contained 10 ml of a YPD liquid medium (containing 100 μg/ml of G418) and shaken for culturing at 28° C. for 3 days (100 cycles/min), and the agglutination was evaluated by visual examination. The evaluation scale for the level of agglutination was according to the scaling method of Johnston, et al. (Yeast Genetics: Fundamental and Applied Aspects, p.205–224, Springer Verlag, N.Y., ed. by J. F. T. Spencer, D. M. Spencer, A. R. W. Smith, 1983).

TABLE 1

Introduction of agglutination genes FL01S and FL01L into various yeasts for practical use and expression thereof

| Type of Yeast/plasmid | | YRpGLF14S | YRpGLF8L |
|---|---|---|---|
| Bottom brewer's yeast | W204 | 4 | 5 |
| | W164 | 4 | 5 |
| | SMA-S | 4 | 5 |
| | H.H. | 4 | 5 |
| Top brewer's yeast | obg. 160 | 2 | 5 |
| Whiskey yeast | AHU3200 | 4 | 5 |
| Wine yeast | IAM4175 | 1 | 3 |
| Japanese sake yeast | Association No. 6 | 4 | 5 |
| Shochu yeast | IFO 0282 | 2 | 4 |
| Alcohol yeast | IFO 0216 | 2 | 4 |

Note:) Evaluation of agglutination shown as 6 levels, 0–5. 0: non-agglutinative, 1: very weakly agglutinative, 2: weakly agglutinative, 3: moderately agglutinative, 4: strongly agglutinative, 5: very strongly agglutinative.

These results show that by introduction of the agglutination genes FL01S and FL01L, it was possible to convert all of the various non-agglutinative industrial yeasts into agglutinative yeasts, although there was some degree of difference in the agglutination. It need not be mentioned that with introduction of the vector plasmid YRpGL10, the host cells remained non-agglutinative.

Furthermore, it was evident that introduction of the FL01L gene produced a stronger agglutinative property in the host strain than did introduction of the FL01S gene.

Example 9

[(Introduction of FL01L gene into various yeast strains for practical use (2: incorporation into yeast chromosomes)]

In general, when exogenous genes are introduced into host cells in the form of plasmids, the plasmids escape from the cells as a result of successive culturing under non-selective pressure. Actually, the plasmids were observed to escape readily from the transformants obtained in Example 8 when selective pressure by G418 was not applied. Here, in order to stably maintain the FL01 gene in the yeasts, the present inventors attempted to incorporate the FL01 gene into the yeast chromosomes.

(i) Preparation of an FL01 expression cassette for incorporation (A flow chart is shown in FIG. 12. The numbers next to each plasmid and open reading frame (ORF) in the flow chart match the numbers next to the plasmids and open reading frames shown in detail in FIGS. 13–27).

For the expression of the FL01 gene in the yeasts at high frequencies, a promotor was incorporated upstream from the 5' end of the open reading frame of the FL01 gene, and a terminator was incorporated downstream from the 3' end thereof, at the unit controlling transcription/translation of the yeast alcohol dehydrogenase gene. That is, the open reading frame sequence of either FL01S or FL01L was inserted at the HindIII site of plasmid pBR-dH-ADH1 which contained the promotor and terminator sequences for the yeast alcohol dehydrogenase gene, to obtain pBR-ADH1-FL01S (FIG. 22) and pBR-ADH1-FL01L (FIG. 27), respectively. The present expression cassette was prepared at the time of preparation of the open reading frame of FL01S using the PCR method (the PCR experiment was the same as in Example 5), and we the present inventors confirmed by the results of restriction enzyme analysis and DNA sequencing that the base sequence of the FL01S gene prepared in this manner was exactly identical to the base sequence shown by the restriction enzyme cleavage map in FIG. 2 obtained from the results of Example 3 and listed as (SEQ ID No: 3).

(ii) Example of incorporation of FL01 expression cassette into brewer's yeast genome by the cotransformation method The cotransformation method of Penttila, et al. (Current Genetics, Vol. 12, p.413–420, 1987) was used to incorporate an FL01 expression cassette which contained no vector-derived sequence (sequence derived from the vector plasmid pBR322) into the chromosomal DNA of the yeast (non-agglutinative bottom brewer's yeast W204). That is, 50 μg of either plasmid pBR-ADH1-FL01S or pBR-ADH1-FL01L obtained above in (i) was digested with restriction enzyme BamHI and subjected to phenol/chloroform treatment, after which 50 μg of the G418-resistant plasmid YRpGL10 was added thereto and they were subjected to precipitation with ethanol. The DNA sample was air-dried, and the yeast was transformed according to the method described above in Example 8. The transformants were selected with G418-resistance as the marker, and the obtained transformants were screened by the microplate assay method (see Example 1) to obtain the agglutinative strain. Here, the details of the microplate assay method are as follows. The resulting transformants were taken up from the plate one at a time using a toothpick, inoculated into a 96-well microplate (each well containing 200 μl of YPD liquid medium), and cultured at 25° C. for 3 days. The determination of agglutination was made by vigorously shaking the microplate for 60 seconds after culturing using a microplate mixer (product of Titech Co.) and then visually locating the agglutinative clones.

The agglutinative strain obtained in this manner was non-selectively cultured for 10–20 generations in a YPD medium, after which the cells were appropriately diluted, applied onto a YPD agar medium, and cultured at 30° C. for 2–3 days. The colony accumulated on the plate was replicated onto one YPD agar medium which contained 200 μg/ml of G418 and another YPD agar medium which contained no G418, and the G418-resistance of the colonies was examined to recover strains which exhibited no G418-resistance. These strains had plasmid YRpGL10 missing from their cells, but it is thought that the FL01 expression cassette (i.e., the open reading frame of the FL01S or FL01L gene under control of expression of the ADH1 promotor and ADH1 terminator) had been incorporated onto the ADH1 locus of the chromosome by in vivo gene replacement using the homologous sequence portion of the ADH1 gene.

Of these, the strain into which the FL01S expression cassette was incorporated was named W204-FL01S, and the strain into which the FL01L expression cassette was incorporated was named W204-FL01L. When these strains were cultured for 50 generations, they still maintained their agglutinative properties at the same levels as prior to culturing. Also, when the W204-FL01S and W204-FL01L strains were subjected to genomic Southern analysis, the present inventors confirmed that all of the FL01 expression cassettes had been incorporated into the chromosomal DNA.

(iii) Fermentation test

A beer fermentation test on as small a scale as 2 liters was conducted using the W204-FL01S and W204-FL01L strains obtained in (ii). That is, the method followed was the standard method of the European Institute of Brewing (Journal of the Institute of Brewing, EBC Analytica Microbiologica, Method 2.5.4., Tubes E.B.C., Vol. 83, p.117–118, 1977). The cells were cultured while standing in 50 ml of wort at 20° C. for 3 days, and the entire amount thereof was added to 1 l of wort and then cultured while standing at 15° C. for 1 week. The grown-up cells were collected by centrifugal separation (5,000 rpm× 10 minutes). The obtained yeast cells were added to wort (with an oxygen concentration of 9 ppm adjusted in advance) at 11° P (plateau degrees) to a concentration of 0.5% (wet v/v). Stationary fermentation was then effected at 10° C. for 10 days. When the amounts of agglutination and sedimentation were compared at this point, the parent strain W204, being non-agglutinative, had a lower amount of settled yeast, and the amount of yeast recovered was roughly the same as the amount of yeast initially added (i.e., 100% recovery). However, the W204-FL01L strain into which the FL01L expression cassette had been incorporated exhibited a strong agglutinative property, and the amount of yeast recovered was twice or more the amount of yeast initially added (i.e., 200% or greater). Nevertheless, the W204-FL01S strain into which the FL01S expression cassette had been incorporated exhibited only a very weak agglutinative property, and the amount of yeast recovered was no more than in the case of W204. It is assumed that this suggests that adequate agglutination of the host cells cannot be induced in wort with the introduction of a single copy of FL01S (With the introduction of multiple copies of FL01S obtained in Example 8, W204 exhibited agglutination even in wort).

Nevertheless, the W204-FL01S strain with a single copy of FL01S introduced onto the chromosome exhibited moderate agglutination in the YPD culture medium, but the reason this was not exhibited in the wort is not clear at the present time.

Also, after completion of the fermentation (pre-fermentation) described above, maturation (after-fermentation) of the supernatant thereof (young beer) was effected. That is, after completion of the process of after-fermentation at 5° C. for 2 weeks and 0° C. for 1 week, the fermentate was subjected to filtration with a membrane filter and carbonation at 0° C., 2 atmospheres for 2 days, after which it was chemically analyzed and taste sampled. The results showed no difference whatsoever between W204 and W204-FL01L. Therefore, by brewing beer using the yeasts according to the present invention, it was made clear that only the agglutinative properties of the yeasts were improved without causing any modification whatsoever to the flavoring components of the control strains.

Deposition

The transformed strain *Escherichia coli* FL01L derived from the introduction of the plasmid pBR-dEP1-FL01L (FIG. 25) containing the DNA chain according to the present invention (open reading frame of the FL01L gene) into *E. coli* strain JA221 was deposited at the MITI National Institute of Bioscience and Human Technology as of Jan. 13, 1993, and has been assigned the Deposit No. FERM BP-4136.

5,585,271

We claim:

1. An agglutination gene encoding the amino acid sequence of SEQ ID NO:1.

2. A plasmid comprising a gene encoding the amino acid sequence of SEQ ID NO:1.

3. A yeast transformed with a plasmid comprising a gene encoding the amino acid sequence of SEQ ID NO:1.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 4614 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Saccharomyces cerevisiae
        ( B ) STRAIN: ABXL-1D ( i x ) FEATURE:
        ( A ) NAME/KEY: CDS
        ( B ) LOCATION: 1..4614

( x i ) SEQUENCE DESCRIPTION: SEQ ID NO:1:

```
ATG ACA ATG CCT CAT CGC TAT ATG TTT TTG GCA GTC TTT ACA CTT CTG        48
Met Thr Met Pro His Arg Tyr Met Phe Leu Ala Val Phe Thr Leu Leu
 1               5                  10                  15

GCA CTA ACT AGT GTG GCC TCA GGA GCC ACA GAG GCG TGC TTA CCA GCA        96
Ala Leu Thr Ser Val Ala Ser Gly Ala Thr Glu Ala Cys Leu Pro Ala
             20                  25                  30

GGC CAG AGG AAA AGT GGG ATG AAT ATA AAT TTT TAC CAG TAT TCA TTG       144
Gly Gln Arg Lys Ser Gly Met Asn Ile Asn Phe Tyr Gln Tyr Ser Leu
         35                  40                  45

AAA GAT TCC TCC ACA TAT TCG AAT GCA GCA TAT ATG GCT TAT GGA TAT       192
Lys Asp Ser Ser Thr Tyr Ser Asn Ala Ala Tyr Met Ala Tyr Gly Tyr
     50                  55                  60

GCC TCA AAA ACC AAA CTA GGT TCT GTC GGA GGA CAA ACT GAT ATC TCG       240
Ala Ser Lys Thr Lys Leu Gly Ser Val Gly Gly Gln Thr Asp Ile Ser
 65                  70                  75                  80

ATT GAT TAT AAT ATT CCC TGT GTT AGT TCA TCA GGC ACA TTT CCT TGT       288
Ile Asp Tyr Asn Ile Pro Cys Val Ser Ser Ser Gly Thr Phe Pro Cys
                 85                  90                  95

CCT CAA GAA GAT TCC TAT GGA AAC TGG GGA TGC AAA GGA ATG GGT GCT       336
Pro Gln Glu Asp Ser Tyr Gly Asn Trp Gly Cys Lys Gly Met Gly Ala
                100                 105                 110

TGT TCT AAT AGT CAA GGA ATT GCA TAC TGG AGT ACT GAT TTA TTT GGT       384
Cys Ser Asn Ser Gln Gly Ile Ala Tyr Trp Ser Thr Asp Leu Phe Gly
            115                 120                 125

TTC TAT ACT ACC CCA ACA AAC GTA ACC CTA GAA ATG ACA GGT TAT TTT       432
Phe Tyr Thr Thr Pro Thr Asn Val Thr Leu Glu Met Thr Gly Tyr Phe
        130                 135                 140

TTA CCA CCA CAG ACG GGT TCT TAC ACA TTC AAG TTT GCT ACA GTT GAC       480
Leu Pro Pro Gln Thr Gly Ser Tyr Thr Phe Lys Phe Ala Thr Val Asp
145                 150                 155                 160

GAC TCT GCA ATT CTA TCA GTA GGT GGT GCA ACC GCG TTC AAC TGT TGT       528
Asp Ser Ala Ile Leu Ser Val Gly Gly Ala Thr Ala Phe Asn Cys Cys
                165                 170                 175

GCT CAA CAG CAA CCG CCG ATC ACA TCA ACG AAC TTT ACC ATT GAC GGT       576
Ala Gln Gln Gln Pro Pro Ile Thr Ser Thr Asn Phe Thr Ile Asp Gly
                180                 185                 190

ATC AAG CCA TGG GGT GGA AGT TTG CCA CCT AAT ATC GAA GGA ACC GTC       624
Ile Lys Pro Trp Gly Gly Ser Leu Pro Pro Asn Ile Glu Gly Thr Val
            195                 200                 205
```

| | | | | | | | | | | | | | | | | |
|---|---|---|---|---|---|---|---|---|---|---|---|---|---|---|---|---|
| TAT | ATG | TAC | GCT | GGC | TAC | TAT | TAT | CCA | ATG | AAG | GTT | GTT | TAC | TCG | AAC | 672 |
| Tyr | Met | Tyr | Ala | Gly | Tyr | Tyr | Tyr | Pro | Met | Lys | Val | Val | Tyr | Ser | Asn | |
| | 210 | | | | 215 | | | | | 220 | | | | | | |
| GCT | GTT | TCT | TGG | GGT | ACA | CTT | CCA | ATT | AGT | GTG | ACA | CTT | CCA | GAT | GGT | 720 |
| Ala | Val | Ser | Trp | Gly | Thr | Leu | Pro | Ile | Ser | Val | Thr | Leu | Pro | Asp | Gly | |
| 225 | | | | | 230 | | | | | 235 | | | | | 240 | |
| ACC | ACT | GTA | AGT | GAT | GAC | TTC | GAA | GGG | TAC | GTC | TAT | TCC | TTT | GAC | GAT | 768 |
| Thr | Thr | Val | Ser | Asp | Asp | Phe | Glu | Gly | Tyr | Val | Tyr | Ser | Phe | Asp | Asp | |
| | | | | 245 | | | | | 250 | | | | | 255 | | |
| GAC | CTA | AGT | CAA | TCT | AAC | TGT | ACT | GTC | CCT | GAC | CCT | TCA | AAT | TAT | GCT | 816 |
| Asp | Leu | Ser | Gln | Ser | Asn | Cys | Thr | Val | Pro | Asp | Pro | Ser | Asn | Tyr | Ala | |
| | | | 260 | | | | | 265 | | | | | 270 | | | |
| GTC | AGT | ACC | ACT | ACA | ACT | ACA | ACG | GAA | CCA | TGG | ACC | GGT | ACT | TTC | ACT | 864 |
| Val | Ser | Thr | Thr | Thr | Thr | Thr | Thr | Glu | Pro | Trp | Thr | Gly | Thr | Phe | Thr | |
| | | 275 | | | | | 280 | | | | | 285 | | | | |
| TCT | ACA | TCT | ACT | GAA | ATG | ACC | ACC | GTC | ACC | GGT | ACC | AAC | GGC | GTT | CCA | 912 |
| Ser | Thr | Ser | Thr | Glu | Met | Thr | Thr | Val | Thr | Gly | Thr | Asn | Gly | Val | Pro | |
| | 290 | | | | | 295 | | | | | 300 | | | | | |
| ACT | GAC | GAA | ACC | GTC | ATT | GTC | ATC | AGA | ACT | CCA | ACA | ACT | GCT | AGC | ACC | 960 |
| Thr | Asp | Glu | Thr | Val | Ile | Val | Ile | Arg | Thr | Pro | Thr | Thr | Ala | Ser | Thr | |
| 305 | | | | | 310 | | | | | 315 | | | | | 320 | |
| ATC | ATA | ACT | ACA | ACT | GAG | CCA | TGG | AAC | AGC | ACT | TTT | ACC | TCT | ACT | TCT | 1008 |
| Ile | Ile | Thr | Thr | Thr | Glu | Pro | Trp | Asn | Ser | Thr | Phe | Thr | Ser | Thr | Ser | |
| | | | | 325 | | | | | 330 | | | | | 335 | | |
| ACC | GAA | TTG | ACC | ACA | GTC | ACT | GGC | ACC | AAT | GGT | GTA | CGA | ACT | GAC | GAA | 1056 |
| Thr | Glu | Leu | Thr | Thr | Val | Thr | Gly | Thr | Asn | Gly | Val | Arg | Thr | Asp | Glu | |
| | | | 340 | | | | | 345 | | | | | 350 | | | |
| ACC | ATC | ATT | GTA | ATC | AGA | ACA | CCA | ACA | ACA | GCC | ACT | ACT | GCC | ATA | ACT | 1104 |
| Thr | Ile | Ile | Val | Ile | Arg | Thr | Pro | Thr | Thr | Ala | Thr | Thr | Ala | Ile | Thr | |
| | | 355 | | | | | 360 | | | | | 365 | | | | |
| ACA | ACT | GAG | CCA | TGG | AAC | AGC | ACT | TTT | ACC | TCT | ACT | TCT | ACC | GAA | TTG | 1152 |
| Thr | Thr | Glu | Pro | Trp | Asn | Ser | Thr | Phe | Thr | Ser | Thr | Ser | Thr | Glu | Leu | |
| | 370 | | | | | 375 | | | | | 380 | | | | | |
| ACC | ACA | GTC | ACC | GGT | ACC | AAT | GGT | TTG | CCA | ACT | GAT | GAG | ACC | ATC | ATT | 1200 |
| Thr | Thr | Val | Thr | Gly | Thr | Asn | Gly | Leu | Pro | Thr | Asp | Glu | Thr | Ile | Ile | |
| 385 | | | | | 390 | | | | | 395 | | | | | 400 | |
| GTC | ATC | AGA | ACA | CCA | ACA | ACA | GCC | ACT | ACT | GCC | ATG | ACT | ACA | ACT | CAG | 1248 |
| Val | Ile | Arg | Thr | Pro | Thr | Thr | Ala | Thr | Thr | Ala | Met | Thr | Thr | Thr | Gln | |
| | | | | 405 | | | | | 410 | | | | | 415 | | |
| CCA | TGG | AAC | GAC | ACT | TTT | ACC | TCT | ACA | TCC | ACT | GAA | ATG | ACC | ACC | GTC | 1296 |
| Pro | Trp | Asn | Asp | Thr | Phe | Thr | Ser | Thr | Ser | Thr | Glu | Met | Thr | Thr | Val | |
| | | | 420 | | | | | 425 | | | | | 430 | | | |
| ACC | GGT | ACC | AAC | GGT | TTG | CCA | ACT | GAT | GAA | ACC | ATC | ATT | GTC | ATC | AGA | 1344 |
| Thr | Gly | Thr | Asn | Gly | Leu | Pro | Thr | Asp | Glu | Thr | Ile | Ile | Val | Ile | Arg | |
| | | 435 | | | | | 440 | | | | | 445 | | | | |
| ACA | CCA | ACA | ACA | GCC | ACT | ACT | GCT | ATG | ACT | ACA | ACT | CAG | CCA | TGG | GAC | 1392 |
| Thr | Pro | Thr | Thr | Ala | Thr | Thr | Ala | Met | Thr | Thr | Thr | Gln | Pro | Trp | Asp | |
| | 450 | | | | | 455 | | | | | 460 | | | | | |
| GAC | ACT | TTT | ACC | TCT | ACA | TCC | ACT | GAA | ATG | ACC | ACC | GTC | ACC | GGT | ACC | 1440 |
| Asp | Thr | Phe | Thr | Ser | Thr | Ser | Thr | Glu | Met | Thr | Thr | Val | Thr | Gly | Thr | |
| 465 | | | | | 470 | | | | | 475 | | | | | 480 | |
| AAC | GGT | TTG | CCA | ACT | GAT | GAA | ACC | ATC | ATT | GTC | ATC | AGA | ACA | CCA | ACA | 1488 |
| Asn | Gly | Leu | Pro | Thr | Asp | Glu | Thr | Ile | Ile | Val | Ile | Arg | Thr | Pro | Thr | |
| | | | | 485 | | | | | 490 | | | | | 495 | | |
| ACA | GCC | ACT | ACT | GCC | ATG | ACT | ACA | ACT | CAG | CCA | TGG | AAC | GAC | ACT | TTT | 1536 |
| Thr | Ala | Thr | Thr | Ala | Met | Thr | Thr | Thr | Gln | Pro | Trp | Asn | Asp | Thr | Phe | |
| | | | 500 | | | | | 505 | | | | | 510 | | | |
| ACC | TCT | ACA | TCC | ACT | GAA | ATG | ACC | ACC | GTC | ACC | GGT | ACC | AAT | GGT | TTG | 1584 |
| Thr | Ser | Thr | Ser | Thr | Glu | Met | Thr | Thr | Val | Thr | Gly | Thr | Asn | Gly | Leu | |
| | | 515 | | | | | 520 | | | | | 525 | | | | |

| | | | | | | | | | | | | | | | |
|---|---|---|---|---|---|---|---|---|---|---|---|---|---|---|---|
| CCA | ACT | GAT | GAG | ACC | ATC | ATT | GTC | ATC | AGA | ACA | CCA | ACA | ACA | GCC | ACT | 1632 |
| Pro | Thr | Asp | Glu | Thr | Ile | Ile | Val | Ile | Arg | Thr | Pro | Thr | Thr | Ala | Thr | |
| | | 530 | | | | 535 | | | | | 540 | | | | | |
| ACT | GCC | ATG | ACT | ACA | ACT | CAG | CCA | TGG | AAC | GAC | ACT | TTT | ACC | TCT | ACA | 1680 |
| Thr | Ala | Met | Thr | Thr | Thr | Gln | Pro | Trp | Asn | Asp | Thr | Phe | Thr | Ser | Thr | |
| 545 | | | | | 550 | | | | | 555 | | | | | 560 | |
| TCC | ACT | GAA | ATG | ACC | ACC | GTC | ACC | GGT | ACC | AAC | GGT | TTG | CCA | ACT | GAT | 1728 |
| Ser | Thr | Glu | Met | Thr | Thr | Val | Thr | Gly | Thr | Asn | Gly | Leu | Pro | Thr | Asp | |
| | | | | 565 | | | | | 570 | | | | | 575 | | |
| GAA | ACC | ATC | ATT | GTC | ATC | AGA | ACA | CCA | ACA | ACA | GCC | ACT | ACT | GCC | ATA | 1776 |
| Glu | Thr | Ile | Ile | Val | Ile | Arg | Thr | Pro | Thr | Thr | Ala | Thr | Thr | Ala | Ile | |
| | | | 580 | | | | | | 585 | | | | 590 | | | |
| ACT | ACA | ACT | GAG | CCA | TGG | AAC | AGC | ACT | TTT | ACC | TCT | ACT | TCT | ACC | GAA | 1824 |
| Thr | Thr | Thr | Glu | Pro | Trp | Asn | Ser | Thr | Phe | Thr | Ser | Thr | Ser | Thr | Glu | |
| | | 595 | | | | | 600 | | | | | 605 | | | | |
| TTG | ACC | ACA | GTC | ACC | GGT | ACC | AAT | GGT | TTG | CCA | ACT | GAT | GAG | ACC | ATC | 1872 |
| Leu | Thr | Thr | Val | Thr | Gly | Thr | Asn | Gly | Leu | Pro | Thr | Asp | Glu | Thr | Ile | |
| | 610 | | | | | 615 | | | | | 620 | | | | | |
| ATT | GTC | ATC | AGA | ACA | CCA | ACA | ACA | GCC | ACT | ACT | GCC | ATG | ACT | ACA | ACT | 1920 |
| Ile | Val | Ile | Arg | Thr | Pro | Thr | Thr | Ala | Thr | Thr | Ala | Met | Thr | Thr | Thr | |
| 625 | | | | | 630 | | | | | 635 | | | | | 640 | |
| CAG | CCA | TGG | AAC | GAC | ACT | TTT | ACC | TCT | ACA | TCC | ACT | GAA | ATG | ACC | ACC | 1968 |
| Gln | Pro | Trp | Asn | Asp | Thr | Phe | Thr | Ser | Thr | Ser | Thr | Glu | Met | Thr | Thr | |
| | | | | 645 | | | | | 650 | | | | | 655 | | |
| GTC | ACC | GGT | ACC | AAC | GGT | TTG | CCA | ACT | GAT | GAA | ACC | ATC | ATT | GTC | ATC | 2016 |
| Val | Thr | Gly | Thr | Asn | Gly | Leu | Pro | Thr | Asp | Glu | Thr | Ile | Ile | Val | Ile | |
| | | 660 | | | | | 665 | | | | | 670 | | | | |
| AGA | ACA | CCA | ACA | ACA | GCC | ACT | ACT | GCC | ATG | ACT | ACA | ACT | CAG | CCA | TGG | 2064 |
| Arg | Thr | Pro | Thr | Thr | Ala | Thr | Thr | Ala | Met | Thr | Thr | Thr | Gln | Pro | Trp | |
| | | 675 | | | | | 680 | | | | | 685 | | | | |
| AAC | GAC | ACT | TTT | ACC | TCT | ACA | TCC | ACT | GAA | ATG | ACC | ACC | GTC | ACC | GGT | 2112 |
| Asn | Asp | Thr | Phe | Thr | Ser | Thr | Ser | Thr | Glu | Met | Thr | Thr | Val | Thr | Gly | |
| | | 690 | | | | | 695 | | | | | 700 | | | | |
| ACC | AAC | GGT | TTG | CCA | ACT | GAT | GAG | ACC | ATC | ATT | GTC | ATC | AGA | ACA | CCA | 2160 |
| Thr | Asn | Gly | Leu | Pro | Thr | Asp | Glu | Thr | Ile | Ile | Val | Ile | Arg | Thr | Pro | |
| 705 | | | | | 710 | | | | | 715 | | | | | 720 | |
| ACA | ACA | GCC | ACT | ACT | GCC | ATG | ACT | ACA | ACT | CAG | CCA | TGG | AAC | GAC | ACT | 2208 |
| Thr | Thr | Ala | Thr | Thr | Ala | Met | Thr | Thr | Thr | Gln | Pro | Trp | Asn | Asp | Thr | |
| | | | | 725 | | | | | 730 | | | | | 735 | | |
| TTT | ACC | TCT | ACA | TCC | ACT | GAA | ATG | ACC | ACC | GTC | ACC | GGT | ACC | AAC | GGC | 2256 |
| Phe | Thr | Ser | Thr | Ser | Thr | Glu | Met | Thr | Thr | Val | Thr | Gly | Thr | Asn | Gly | |
| | | | 740 | | | | | 745 | | | | | 750 | | | |
| GTT | CCA | ACT | GAC | GAA | ACC | GTC | ATT | GTC | ATC | AGA | ACT | CCA | ACT | AGT | GAA | 2304 |
| Val | Pro | Thr | Asp | Glu | Thr | Val | Ile | Val | Ile | Arg | Thr | Pro | Thr | Ser | Glu | |
| | | 755 | | | | | 760 | | | | | 765 | | | | |
| GGT | CTA | ATC | AGC | ACC | ACC | ACT | GAA | CCA | TGG | ACT | GGT | ACT | TTC | ACC | TCT | 2352 |
| Gly | Leu | Ile | Ser | Thr | Thr | Thr | Glu | Pro | Trp | Thr | Gly | Thr | Phe | Thr | Ser | |
| | 770 | | | | | 775 | | | | | 780 | | | | | |
| ACA | TCC | ACT | GAG | ATG | ACC | ACC | GTC | ACC | GGT | ACT | AAC | GGT | CAA | CCA | ACT | 2400 |
| Thr | Ser | Thr | Glu | Met | Thr | Thr | Val | Thr | Gly | Thr | Asn | Gly | Gln | Pro | Thr | |
| 785 | | | | | 790 | | | | | 795 | | | | | 800 | |
| GAC | GAA | ACC | GTG | ATT | GTT | ATC | AGA | ACT | CCA | ACC | AGT | GAA | GGT | TTG | GTT | 2448 |
| Asp | Glu | Thr | Val | Ile | Val | Ile | Arg | Thr | Pro | Thr | Ser | Glu | Gly | Leu | Val | |
| | | | | 805 | | | | | 810 | | | | | 815 | | |
| ACA | ACC | ACC | ACT | GAA | CCA | TGG | ACT | GGT | ACT | TTT | ACT | TCT | ACA | TCT | ACT | 2496 |
| Thr | Thr | Thr | Thr | Glu | Pro | Trp | Thr | Gly | Thr | Phe | Thr | Ser | Thr | Ser | Thr | |
| | | | 820 | | | | | 825 | | | | | 830 | | | |
| GAA | ATG | ACC | ACC | ATT | ACT | GGA | ACC | AAC | GGC | GTT | CCA | ACT | GAC | GAA | ACC | 2544 |
| Glu | Met | Thr | Thr | Ile | Thr | Gly | Thr | Asn | Gly | Val | Pro | Thr | Asp | Glu | Thr | |
| | | 835 | | | | | 840 | | | | | 845 | | | | |

| | | | | | | | | | | | | | | | | |
|---|---|---|---|---|---|---|---|---|---|---|---|---|---|---|---|---|
| GTC | ATT | GTC | ATC | AGA | ACT | CCA | ACC | AGT | GAA | GGT | CTA | ATC | AGC | ACC | ACC | 2592 |
| Val | Ile | Val | Ile | Arg | Thr | Pro | Thr | Ser | Glu | Gly | Leu | Ile | Ser | Thr | Thr | |
| | 850 | | | | | 855 | | | | | 860 | | | | | |
| ACT | GAA | CCA | TGG | ACT | GGT | ACT | TTT | ACT | TCT | ACA | TCT | ACT | GAA | ATG | ACC | 2640 |
| Thr | Glu | Pro | Trp | Thr | Gly | Thr | Phe | Thr | Ser | Thr | Ser | Thr | Glu | Met | Thr | |
| 865 | | | | 870 | | | | | 875 | | | | | | 880 | |
| ACC | ATT | ACT | GGA | ACC | AAT | GGT | CAA | CCA | ACT | GAC | GAA | ACC | GTT | ATT | GTT | 2688 |
| Thr | Ile | Thr | Gly | Thr | Asn | Gly | Gln | Pro | Thr | Asp | Glu | Thr | Val | Ile | Val | |
| | | | | 885 | | | | | 890 | | | | | 895 | | |
| ATC | AGA | ACT | CCA | ACT | AGT | GAA | GGT | CTA | ATC | AGC | ACC | ACC | ACT | GAA | CCA | 2736 |
| Ile | Arg | Thr | Pro | Thr | Ser | Glu | Gly | Leu | Ile | Ser | Thr | Thr | Thr | Glu | Pro | |
| | | | 900 | | | | | 905 | | | | | 910 | | | |
| TGG | ACT | GGT | ACT | TTC | ACT | TCT | ACA | TCT | ACT | GAA | ATG | ACC | ACC | GTC | ACC | 2784 |
| Trp | Thr | Gly | Thr | Phe | Thr | Ser | Thr | Ser | Thr | Glu | Met | Thr | Thr | Val | Thr | |
| | | 915 | | | | | 920 | | | | | 925 | | | | |
| GGT | ACC | AAC | GGC | GTT | CCA | ACT | GAC | GAA | ACC | GTC | ATT | GTC | ATC | AGA | ACT | 2832 |
| Gly | Thr | Asn | Gly | Val | Pro | Thr | Asp | Glu | Thr | Val | Ile | Val | Ile | Arg | Thr | |
| 930 | | | | | 935 | | | | | 940 | | | | | | |
| CCA | ACC | AGT | GAA | GGT | CTA | ATC | AGC | ACC | ACC | ACT | GAA | CCA | TGG | ACT | GGC | 2880 |
| Pro | Thr | Ser | Glu | Gly | Leu | Ile | Ser | Thr | Thr | Thr | Glu | Pro | Trp | Thr | Gly | |
| 945 | | | | | 950 | | | | | 955 | | | | | 960 | |
| ACT | TTC | ACT | TCG | ACT | TCC | ACT | GAG | GTT | ACC | ACC | ATC | ACT | GGA | ACC | AAC | 2928 |
| Thr | Phe | Thr | Ser | Thr | Ser | Thr | Glu | Val | Thr | Thr | Ile | Thr | Gly | Thr | Asn | |
| | | | | 965 | | | | | 970 | | | | | | 975 | |
| GGT | CAA | CCA | ACT | GAC | GAA | ACT | GTG | ATT | GTT | ATC | AGA | ACT | CCA | ACC | AGT | 2976 |
| Gly | Gln | Pro | Thr | Asp | Glu | Thr | Val | Ile | Val | Ile | Arg | Thr | Pro | Thr | Ser | |
| | | | | 980 | | | | | 985 | | | | | 990 | | |
| GAA | GGT | CTA | ATC | AGC | ACC | ACC | ACT | GAA | CCA | TGG | ACT | GGT | ACT | TTC | ACT | 3024 |
| Glu | Gly | Leu | Ile | Ser | Thr | Thr | Thr | Glu | Pro | Trp | Thr | Gly | Thr | Phe | Thr | |
| | | | 995 | | | | | 1000 | | | | | 1005 | | | |
| TCT | ACA | TCT | ACT | GAA | ATG | ACC | ACC | GTC | ACC | GGT | ACT | AAC | GGT | CAA | CCA | 3072 |
| Ser | Thr | Ser | Thr | Glu | Met | Thr | Thr | Val | Thr | Gly | Thr | Asn | Gly | Gln | Pro | |
| | | 1010 | | | | | 1015 | | | | | 1020 | | | | |
| ACT | GAC | GAA | ACC | GTG | ATT | GTT | ATC | AGA | ACT | CCA | ACC | AGT | GAA | GGT | TTG | 3120 |
| Thr | Asp | Glu | Thr | Val | Ile | Val | Ile | Arg | Thr | Pro | Thr | Ser | Glu | Gly | Leu | |
| 1025 | | | | | 1030 | | | | | 1035 | | | | | 1040 | |
| GTT | ACA | ACC | ACC | ACT | GAA | CCA | TGG | ACT | GGT | ACT | TTT | ACT | TCG | ACT | TCC | 3168 |
| Val | Thr | Thr | Thr | Thr | Glu | Pro | Trp | Thr | Gly | Thr | Phe | Thr | Ser | Thr | Ser | |
| | | | | 1045 | | | | | 1050 | | | | | 1055 | | |
| ACT | GAA | ATG | TCT | ACT | GTC | ACT | GGA | ACC | AAT | GGC | TTG | CCA | ACT | GAT | GAA | 3216 |
| Thr | Glu | Met | Ser | Thr | Val | Thr | Gly | Thr | Asn | Gly | Leu | Pro | Thr | Asp | Glu | |
| | | | 1060 | | | | | 1065 | | | | | 1070 | | | |
| ACT | GTC | ATT | GTT | GTC | AAA | ACT | CCA | ACT | ACT | GCC | ATC | TCA | TCC | AGT | TTG | 3264 |
| Thr | Val | Ile | Val | Val | Lys | Thr | Pro | Thr | Thr | Ala | Ile | Ser | Ser | Ser | Leu | |
| | | 1075 | | | | | 1080 | | | | | 1085 | | | | |
| TCA | TCA | TCA | TCT | TCA | GGA | CAA | ATC | ACC | AGC | TCT | ATC | ACG | TCT | TCG | CGT | 3312 |
| Ser | Ser | Ser | Ser | Ser | Gly | Gln | Ile | Thr | Ser | Ser | Ile | Thr | Ser | Ser | Arg | |
| | 1090 | | | | | 1095 | | | | | 1100 | | | | | |
| CCA | ATT | ATT | ACC | CCA | TTC | TAT | CCT | AGC | AAT | GGA | ACT | TCT | GTG | ATT | TCT | 3360 |
| Pro | Ile | Ile | Thr | Pro | Phe | Tyr | Pro | Ser | Asn | Gly | Thr | Ser | Val | Ile | Ser | |
| 1105 | | | | | 1110 | | | | | 1115 | | | | | 1120 | |
| TCC | TCA | GTA | ATT | TCT | TCC | TCA | GTC | ACT | TCT | TCT | CTA | TTC | ACT | TCT | TCT | 3408 |
| Ser | Ser | Val | Ile | Ser | Ser | Ser | Val | Thr | Ser | Ser | Leu | Phe | Thr | Ser | Ser | |
| | | | | 1125 | | | | | 1130 | | | | | 1135 | | |
| CCA | GTC | ATT | TCT | TCC | TCA | GTC | ATT | TCT | TCT | TCT | ACA | ACA | ACC | TCC | ACT | 3456 |
| Pro | Val | Ile | Ser | Ser | Ser | Val | Ile | Ser | Ser | Ser | Thr | Thr | Thr | Ser | Thr | |
| | | | 1140 | | | | | 1145 | | | | | 1150 | | | |
| TCT | ATA | TTT | TCT | GAA | TCA | TCT | AAA | TCA | TCC | GTC | ATT | CCA | ACC | AGT | AGT | 3504 |
| Ser | Ile | Phe | Ser | Glu | Ser | Ser | Lys | Ser | Ser | Val | Ile | Pro | Thr | Ser | Ser | |
| | | 1155 | | | | | 1160 | | | | | 1165 | | | | |

| | | | | | | | | | | | | | | | | |
|---|---|---|---|---|---|---|---|---|---|---|---|---|---|---|---|---|
| TCC | ACC | TCT | GGT | TCT | TCT | GAG | AGC | GAA | ACG | AGT | TCA | GCT | GGT | TCT | GTC | 3552 |
| Ser | Thr | Ser | Gly | Ser | Ser | Glu | Ser | Glu | Thr | Ser | Ser | Ala | Gly | Ser | Val | |
| | | 1170 | | | | 1175 | | | | | 1180 | | | | | |
| TCT | TCT | TCC | TCT | TTT | ATC | TCT | TCT | GAA | TCA | TCA | AAA | TCT | CCT | ACA | TAT | 3600 |
| Ser | Ser | Ser | Ser | Phe | Ile | Ser | Ser | Glu | Ser | Ser | Lys | Ser | Pro | Thr | Tyr | |
| 1185 | | | | | 1190 | | | | | 1195 | | | | | 1200 | |
| TCT | TCT | TCA | TCA | TTA | CCA | CTT | GTT | ACC | AGT | GCG | ACA | ACA | AGC | CAG | GAA | 3648 |
| Ser | Ser | Ser | Ser | Leu | Pro | Leu | Val | Thr | Ser | Ala | Thr | Thr | Ser | Gln | Glu | |
| | | | | 1205 | | | | | 1210 | | | | | 1215 | | |
| ACT | GCT | TCT | TCA | TTA | CCA | CCT | GCT | ACC | ACT | ACA | AAA | ACG | AGC | GAA | CAA | 3696 |
| Thr | Ala | Ser | Ser | Leu | Pro | Pro | Ala | Thr | Thr | Thr | Lys | Thr | Ser | Glu | Gln | |
| | | | 1220 | | | | | 1225 | | | | | 1230 | | | |
| ACC | ACT | TTG | GTT | ACC | GTG | ACA | TCC | TGC | GAG | TCT | CAT | GTG | TGC | ACT | GAA | 3744 |
| Thr | Thr | Leu | Val | Thr | Val | Thr | Ser | Cys | Glu | Ser | His | Val | Cys | Thr | Glu | |
| | | 1235 | | | | | 1240 | | | | | 1245 | | | | |
| TCC | ATC | TCC | CCT | GCG | ATT | GTT | TCC | ACA | GCT | ACT | GTT | ACT | GTT | AGC | GGC | 3792 |
| Ser | Ile | Ser | Pro | Ala | Ile | Val | Ser | Thr | Ala | Thr | Val | Thr | Val | Ser | Gly | |
| | 1250 | | | | | 1255 | | | | | 1260 | | | | | |
| GTC | ACA | ACA | GAG | TAT | ACC | ACA | TGG | TGC | CCT | ATT | TCT | ACT | ACA | GAG | ACA | 3840 |
| Val | Thr | Thr | Glu | Tyr | Thr | Thr | Trp | Cys | Pro | Ile | Ser | Thr | Thr | Glu | Thr | |
| 1265 | | | | | 1270 | | | | | 1275 | | | | | 1280 | |
| ACA | AAG | CAA | ACC | AAA | GGG | ACA | ACA | GAG | CAA | ACC | ACA | GAA | ACA | ACA | AAA | 3888 |
| Thr | Lys | Gln | Thr | Lys | Gly | Thr | Thr | Glu | Gln | Thr | Thr | Glu | Thr | Thr | Lys | |
| | | | | 1285 | | | | | 1290 | | | | | 1295 | | |
| CAA | ACC | ACG | GTA | GTT | ACA | ATT | TCT | TCT | TGT | GAA | TCT | GAC | GTA | TGC | TCT | 3936 |
| Gln | Thr | Thr | Val | Val | Thr | Ile | Ser | Ser | Cys | Glu | Ser | Asp | Val | Cys | Ser | |
| | | | 1300 | | | | | 1305 | | | | | 1310 | | | |
| AAG | ACT | GCT | TCT | CCA | GCC | ATT | GTA | TCT | ACA | AGC | ACT | GCT | ACT | ATT | AAC | 3984 |
| Lys | Thr | Ala | Ser | Pro | Ala | Ile | Val | Ser | Thr | Ser | Thr | Ala | Thr | Ile | Asn | |
| | | | 1315 | | | | | 1320 | | | | | 1325 | | | |
| GGC | GTT | ACT | ACA | GAA | TAC | ACA | ACA | TGG | TGT | CCT | ATT | TCC | ACC | ACA | GAA | 4032 |
| Gly | Val | Thr | Thr | Glu | Tyr | Thr | Thr | Trp | Cys | Pro | Ile | Ser | Thr | Thr | Glu | |
| 1330 | | | | | 1335 | | | | | 1340 | | | | | | |
| TCG | AGG | CAA | CAA | ACA | ACG | CTA | GTT | ACT | GTT | ACT | TCC | TGC | GAA | TCT | GGT | 4080 |
| Ser | Arg | Gln | Gln | Thr | Thr | Leu | Val | Thr | Val | Thr | Ser | Cys | Glu | Ser | Gly | |
| 1345 | | | | | 1350 | | | | | 1355 | | | | | 1360 | |
| GTG | TGT | TCC | GAA | ACT | GCT | TCA | CCT | GCC | ATT | GTT | TCG | ACG | GCC | ACG | GCT | 4128 |
| Val | Cys | Ser | Glu | Thr | Ala | Ser | Pro | Ala | Ile | Val | Ser | Thr | Ala | Thr | Ala | |
| | | | | 1365 | | | | | 1370 | | | | | 1375 | | |
| ACT | GTG | AAT | GAT | GTT | GTT | ACG | GTC | TAT | CCT | ACA | TGG | AGG | CCA | CAG | ACT | 4176 |
| Thr | Val | Asn | Asp | Val | Val | Thr | Val | Tyr | Pro | Thr | Trp | Arg | Pro | Gln | Thr | |
| | | | 1380 | | | | | 1385 | | | | | 1390 | | | |
| GCG | AAT | GAA | GAG | TCT | GTC | AGC | TCT | AAA | ATG | AAC | AGT | GCT | ACC | GGT | GAG | 4224 |
| Ala | Asn | Glu | Glu | Ser | Val | Ser | Ser | Lys | Met | Asn | Ser | Ala | Thr | Gly | Glu | |
| | | | 1395 | | | | | 1400 | | | | | 1405 | | | |
| ACA | ACA | ACC | AAT | ACT | TTA | GCT | GCT | GAA | ACG | ACT | ACC | AAT | ACT | GTA | GCT | 4272 |
| Thr | Thr | Thr | Asn | Thr | Leu | Ala | Ala | Glu | Thr | Thr | Thr | Asn | Thr | Val | Ala | |
| | 1410 | | | | | 1415 | | | | | 1420 | | | | | |
| GCT | GAG | ACG | ATT | ACC | AAT | ACT | GGA | GCT | GCT | GAG | ACG | AAA | ACA | GTA | GTC | 4320 |
| Ala | Glu | Thr | Ile | Thr | Asn | Thr | Gly | Ala | Ala | Glu | Thr | Lys | Thr | Val | Val | |
| 1425 | | | | | 1430 | | | | | 1435 | | | | | 1440 | |
| ACC | TCT | TCG | CTT | TCA | AGA | TCT | AAT | CAC | GCT | GAA | ACA | CAG | ACG | GCT | TCC | 4368 |
| Thr | Ser | Ser | Leu | Ser | Arg | Ser | Asn | His | Ala | Glu | Thr | Gln | Thr | Ala | Ser | |
| | | | | 1445 | | | | | 1450 | | | | | 1455 | | |
| GCG | ACC | GAT | GTG | ATT | GGT | CAC | AGC | AGT | AGT | GTT | GTT | TCT | GTA | TCC | GAA | 4416 |
| Ala | Thr | Asp | Val | Ile | Gly | His | Ser | Ser | Ser | Val | Val | Ser | Val | Ser | Glu | |
| | | | 1460 | | | | | 1465 | | | | | 1470 | | | |
| ACT | GGC | AAC | ACC | AAG | AGT | CTA | ACA | AGT | TCC | GGG | TTG | AGT | ACT | ATG | TCG | 4464 |
| Thr | Gly | Asn | Thr | Lys | Ser | Leu | Thr | Ser | Ser | Gly | Leu | Ser | Thr | Met | Ser | |
| | | | 1475 | | | | | 1480 | | | | | 1485 | | | |

| CAA Gln 1490 | CAG Gln | CCT Pro | CGT Arg | AGC Ser | ACA Thr | CCA Pro 1495 | GCA Ala | AGC Ser | AGC Ser | ATG Met | GTA Val 1500 | GGA Gly | TAT Tyr | AGT Ser | ACA Thr | 4512 |
| GCT Ala 1505 | TCT Ser | TTA Leu | GAA Glu | ATT Ile | TCA Ser | ACG Thr 1510 | TAT Tyr | GCT Ala | GGC Gly | AGT Ser | GCC Ala 1515 | AAC Asn | AGC Ser | TTA Leu | CTG Leu 1520 | 4560 |
| GCC Ala | GGT Gly | AGT Ser | GGT Gly | TTA Leu 1525 | AGT Ser | GTC Val | TTC Phe | ATT Ile | GCG Ala 1530 | TCC Ser | TTA Leu | TTG Leu | CTG Leu | GCA Ala 1535 | ATT Ile | 4608 |
| ATT Ile | TAA * | | | | | | | | | | | | | | | 4614 |

( 2 ) INFORMATION FOR SEQ ID NO:2:

( i ) SEQUENCE CHARACTERISTICS:
        ( A ) LENGTH: 1537 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Met  Pro  His  Arg  Tyr  Met  Phe  Leu  Ala  Val  Phe  Thr  Leu  Leu
 1              5                        10                       15

Ala  Leu  Thr  Ser  Val  Ala  Ser  Gly  Ala  Thr  Glu  Ala  Cys  Leu  Pro  Ala
              20                        25                       30

Gly  Gln  Arg  Lys  Ser  Gly  Met  Asn  Ile  Asn  Phe  Tyr  Gln  Tyr  Ser  Leu
              35                        40                       45

Lys  Asp  Ser  Ser  Thr  Tyr  Ser  Asn  Ala  Ala  Tyr  Met  Ala  Tyr  Gly  Tyr
         50                        55                       60

Ala  Ser  Lys  Thr  Lys  Leu  Gly  Ser  Val  Gly  Gly  Gln  Thr  Asp  Ile  Ser
65                        70                        75                       80

Ile  Asp  Tyr  Asn  Ile  Pro  Cys  Val  Ser  Ser  Gly  Thr  Phe  Pro  Cys
                   85                        90                       95

Pro  Gln  Glu  Asp  Ser  Tyr  Gly  Asn  Trp  Gly  Cys  Lys  Gly  Met  Gly  Ala
              100                       105                      110

Cys  Ser  Asn  Ser  Gln  Gly  Ile  Ala  Tyr  Trp  Ser  Thr  Asp  Leu  Phe  Gly
              115                       120                      125

Phe  Tyr  Thr  Thr  Pro  Thr  Asn  Val  Thr  Leu  Glu  Met  Thr  Gly  Tyr  Phe
         130                       135                      140

Leu  Pro  Pro  Gln  Thr  Gly  Ser  Tyr  Thr  Phe  Lys  Phe  Ala  Thr  Val  Asp
145                       150                       155                      160

Asp  Ser  Ala  Ile  Leu  Ser  Val  Gly  Gly  Ala  Thr  Ala  Phe  Asn  Cys  Cys
                   165                       170                      175

Ala  Gln  Gln  Gln  Pro  Pro  Ile  Thr  Ser  Thr  Asn  Phe  Thr  Ile  Asp  Gly
              180                       185                      190

Ile  Lys  Pro  Trp  Gly  Gly  Ser  Leu  Pro  Pro  Asn  Ile  Glu  Gly  Thr  Val
         195                       200                      205

Tyr  Met  Tyr  Ala  Gly  Tyr  Tyr  Tyr  Pro  Met  Lys  Val  Val  Tyr  Ser  Asn
         210                       215                      220

Ala  Val  Ser  Trp  Gly  Thr  Leu  Pro  Ile  Ser  Val  Thr  Leu  Pro  Asp  Gly
225                       230                       235                      240

Thr  Thr  Val  Ser  Asp  Asp  Phe  Glu  Gly  Tyr  Val  Tyr  Ser  Phe  Asp  Asp
                   245                       250                      255

Asp  Leu  Ser  Gln  Ser  Asn  Cys  Thr  Val  Pro  Asp  Pro  Ser  Asn  Tyr  Ala
              260                       265                      270

Val  Ser  Thr  Thr  Thr  Thr  Thr  Thr  Glu  Pro  Trp  Thr  Gly  Thr  Phe  Thr
              275                       280                      285
```

| Ser | Thr | Ser | Thr | Glu | Met | Thr | Thr | Val | Thr | Gly | Thr | Asn | Gly | Val | Pro |
|---|---|---|---|---|---|---|---|---|---|---|---|---|---|---|---|
|  | 290 |  |  |  | 295 |  |  |  |  | 300 |  |  |  |  |  |

| Thr | Asp | Glu | Thr | Val | Ile | Val | Ile | Arg | Thr | Pro | Thr | Thr | Ala | Ser | Thr |
|---|---|---|---|---|---|---|---|---|---|---|---|---|---|---|---|
| 305 |  |  |  |  | 310 |  |  |  |  | 315 |  |  |  |  | 320 |

| Ile | Ile | Thr | Thr | Thr | Glu | Pro | Trp | Asn | Ser | Thr | Phe | Thr | Ser | Thr | Ser |
|---|---|---|---|---|---|---|---|---|---|---|---|---|---|---|---|
|  |  |  |  | 325 |  |  |  |  | 330 |  |  |  |  | 335 |  |

| Thr | Glu | Leu | Thr | Thr | Val | Thr | Gly | Thr | Asn | Gly | Val | Arg | Thr | Asp | Glu |
|---|---|---|---|---|---|---|---|---|---|---|---|---|---|---|---|
|  |  |  | 340 |  |  |  |  | 345 |  |  |  |  | 350 |  |  |

| Thr | Ile | Ile | Val | Ile | Arg | Thr | Pro | Thr | Thr | Ala | Thr | Thr | Ala | Ile | Thr |
|---|---|---|---|---|---|---|---|---|---|---|---|---|---|---|---|
|  |  | 355 |  |  |  |  | 360 |  |  |  |  | 365 |  |  |  |

| Thr | Thr | Glu | Pro | Trp | Asn | Ser | Thr | Phe | Thr | Ser | Thr | Ser | Thr | Glu | Leu |
|---|---|---|---|---|---|---|---|---|---|---|---|---|---|---|---|
|  | 370 |  |  |  |  | 375 |  |  |  |  | 380 |  |  |  |  |

| Thr | Thr | Val | Thr | Gly | Thr | Asn | Gly | Leu | Pro | Thr | Asp | Glu | Thr | Ile | Ile |
|---|---|---|---|---|---|---|---|---|---|---|---|---|---|---|---|
| 385 |  |  |  |  | 390 |  |  |  |  | 395 |  |  |  |  | 400 |

| Val | Ile | Arg | Thr | Pro | Thr | Thr | Ala | Thr | Thr | Ala | Met | Thr | Thr | Thr | Gln |
|---|---|---|---|---|---|---|---|---|---|---|---|---|---|---|---|
|  |  |  |  | 405 |  |  |  |  | 410 |  |  |  |  | 415 |  |

| Pro | Trp | Asn | Asp | Thr | Phe | Thr | Ser | Thr | Ser | Thr | Glu | Met | Thr | Thr | Val |
|---|---|---|---|---|---|---|---|---|---|---|---|---|---|---|---|
|  |  |  | 420 |  |  |  |  | 425 |  |  |  |  | 430 |  |  |

| Thr | Gly | Thr | Asn | Gly | Leu | Pro | Thr | Asp | Glu | Thr | Ile | Ile | Val | Ile | Arg |
|---|---|---|---|---|---|---|---|---|---|---|---|---|---|---|---|
|  |  | 435 |  |  |  |  | 440 |  |  |  |  | 445 |  |  |  |

| Thr | Pro | Thr | Thr | Ala | Thr | Thr | Ala | Met | Thr | Thr | Thr | Gln | Pro | Trp | Asp |
|---|---|---|---|---|---|---|---|---|---|---|---|---|---|---|---|
|  | 450 |  |  |  |  | 455 |  |  |  |  | 460 |  |  |  |  |

| Asp | Thr | Phe | Thr | Ser | Thr | Ser | Thr | Glu | Met | Thr | Thr | Val | Thr | Gly | Thr |
|---|---|---|---|---|---|---|---|---|---|---|---|---|---|---|---|
| 465 |  |  |  |  | 470 |  |  |  |  | 475 |  |  |  |  | 480 |

| Asn | Gly | Leu | Pro | Thr | Asp | Glu | Thr | Ile | Ile | Val | Ile | Arg | Thr | Pro | Thr |
|---|---|---|---|---|---|---|---|---|---|---|---|---|---|---|---|
|  |  |  |  | 485 |  |  |  |  | 490 |  |  |  |  | 495 |  |

| Thr | Ala | Thr | Thr | Ala | Met | Thr | Thr | Thr | Gln | Pro | Trp | Asn | Asp | Thr | Phe |
|---|---|---|---|---|---|---|---|---|---|---|---|---|---|---|---|
|  |  |  | 500 |  |  |  |  | 505 |  |  |  |  | 510 |  |  |

| Thr | Ser | Thr | Ser | Thr | Glu | Met | Thr | Thr | Val | Thr | Gly | Thr | Asn | Gly | Leu |
|---|---|---|---|---|---|---|---|---|---|---|---|---|---|---|---|
|  |  | 515 |  |  |  |  | 520 |  |  |  |  | 525 |  |  |  |

| Pro | Thr | Asp | Glu | Thr | Ile | Ile | Val | Ile | Arg | Thr | Pro | Thr | Thr | Ala | Thr |
|---|---|---|---|---|---|---|---|---|---|---|---|---|---|---|---|
|  | 530 |  |  |  |  | 535 |  |  |  |  | 540 |  |  |  |  |

| Thr | Ala | Met | Thr | Thr | Thr | Gln | Pro | Trp | Asn | Asp | Thr | Phe | Thr | Ser | Thr |
|---|---|---|---|---|---|---|---|---|---|---|---|---|---|---|---|
| 545 |  |  |  |  | 550 |  |  |  |  | 555 |  |  |  |  | 560 |

| Ser | Thr | Glu | Met | Thr | Thr | Val | Thr | Gly | Thr | Asn | Gly | Leu | Pro | Thr | Asp |
|---|---|---|---|---|---|---|---|---|---|---|---|---|---|---|---|
|  |  |  |  | 565 |  |  |  |  | 570 |  |  |  |  | 575 |  |

| Glu | Thr | Ile | Ile | Val | Ile | Arg | Thr | Pro | Thr | Thr | Ala | Thr | Thr | Ala | Ile |
|---|---|---|---|---|---|---|---|---|---|---|---|---|---|---|---|
|  |  |  | 580 |  |  |  |  | 585 |  |  |  |  | 590 |  |  |

| Thr | Thr | Thr | Glu | Pro | Trp | Asn | Ser | Thr | Phe | Thr | Ser | Thr | Ser | Thr | Glu |
|---|---|---|---|---|---|---|---|---|---|---|---|---|---|---|---|
|  |  | 595 |  |  |  |  | 600 |  |  |  |  | 605 |  |  |  |

| Leu | Thr | Thr | Val | Thr | Gly | Thr | Asn | Gly | Leu | Pro | Thr | Asp | Glu | Thr | Ile |
|---|---|---|---|---|---|---|---|---|---|---|---|---|---|---|---|
|  | 610 |  |  |  |  | 615 |  |  |  |  | 620 |  |  |  |  |

| Ile | Val | Ile | Arg | Thr | Pro | Thr | Thr | Ala | Thr | Thr | Ala | Met | Thr | Thr | Thr |
|---|---|---|---|---|---|---|---|---|---|---|---|---|---|---|---|
| 625 |  |  |  |  | 630 |  |  |  |  | 635 |  |  |  |  | 640 |

| Gln | Pro | Trp | Asn | Asp | Thr | Phe | Thr | Ser | Thr | Ser | Thr | Glu | Met | Thr | Thr |
|---|---|---|---|---|---|---|---|---|---|---|---|---|---|---|---|
|  |  |  |  | 645 |  |  |  |  | 650 |  |  |  |  | 655 |  |

| Val | Thr | Gly | Thr | Asn | Gly | Leu | Pro | Thr | Asp | Glu | Thr | Ile | Ile | Val | Ile |
|---|---|---|---|---|---|---|---|---|---|---|---|---|---|---|---|
|  |  |  | 660 |  |  |  |  | 665 |  |  |  |  | 670 |  |  |

| Arg | Thr | Pro | Thr | Thr | Ala | Thr | Thr | Ala | Met | Thr | Thr | Thr | Gln | Pro | Trp |
|---|---|---|---|---|---|---|---|---|---|---|---|---|---|---|---|
|  |  | 675 |  |  |  |  | 680 |  |  |  |  | 685 |  |  |  |

| Asn | Asp | Thr | Phe | Thr | Ser | Thr | Ser | Thr | Glu | Met | Thr | Thr | Val | Thr | Gly |
|---|---|---|---|---|---|---|---|---|---|---|---|---|---|---|---|
|  | 690 |  |  |  |  | 695 |  |  |  |  | 700 |  |  |  |  |

| Thr | Asn | Gly | Leu | Pro | Thr | Asp | Glu | Thr | Ile | Ile | Val | Ile | Arg | Thr | Pro |
|---|---|---|---|---|---|---|---|---|---|---|---|---|---|---|---|

| 705 | | | | 710 | | | | 715 | | | | 720 |
|---|---|---|---|---|---|---|---|---|---|---|---|---|
| Thr | Thr | Ala | Thr | Thr | Ala | Met | Thr | Thr | Gln | Pro | Trp | Asn | Asp | Thr |
| | | | | 725 | | | | 730 | | | | 735 | | |
| Phe | Thr | Ser | Thr | Ser | Thr | Glu | Met | Thr | Thr | Val | Thr | Gly | Thr | Asn | Gly |
| | | | 740 | | | | 745 | | | | 750 | | | |
| Val | Pro | Thr | Asp | Glu | Thr | Val | Ile | Val | Ile | Arg | Thr | Pro | Thr | Ser | Glu |
| | | 755 | | | | 760 | | | | 765 | | | | |
| Gly | Leu | Ile | Ser | Thr | Thr | Thr | Glu | Pro | Trp | Thr | Gly | Thr | Phe | Thr | Ser |
| | 770 | | | | 775 | | | | 780 | | | | | |
| Thr | Ser | Thr | Glu | Met | Thr | Thr | Val | Thr | Gly | Thr | Asn | Gly | Gln | Pro | Thr |
| 785 | | | | 790 | | | | 795 | | | | | | 800 |
| Asp | Glu | Thr | Val | Ile | Val | Ile | Arg | Thr | Pro | Thr | Ser | Glu | Gly | Leu | Val |
| | | | | 805 | | | | 810 | | | | | 815 | |
| Thr | Thr | Thr | Thr | Glu | Pro | Trp | Thr | Gly | Thr | Phe | Thr | Ser | Thr | Ser | Thr |
| | | | 820 | | | | | 825 | | | | 830 | | |
| Glu | Met | Thr | Thr | Ile | Thr | Gly | Thr | Asn | Gly | Val | Pro | Thr | Asp | Glu | Thr |
| | | 835 | | | | | 840 | | | | 845 | | | |
| Val | Ile | Val | Ile | Arg | Thr | Pro | Thr | Ser | Glu | Gly | Leu | Ile | Ser | Thr | Thr |
| | 850 | | | | 855 | | | | 860 | | | | | |
| Thr | Glu | Pro | Trp | Thr | Gly | Thr | Phe | Thr | Ser | Ser | Thr | Glu | Met | Thr |
| 865 | | | | | 870 | | | | 875 | | | | 880 |
| Thr | Ile | Thr | Gly | Thr | Asn | Gly | Gln | Pro | Thr | Asp | Glu | Thr | Val | Ile | Val |
| | | | 885 | | | | 890 | | | | 895 | | |
| Ile | Arg | Thr | Pro | Thr | Ser | Glu | Gly | Leu | Ile | Ser | Thr | Thr | Thr | Glu | Pro |
| | | 900 | | | | 905 | | | | 910 | | | | |
| Trp | Thr | Gly | Thr | Phe | Thr | Ser | Thr | Ser | Thr | Glu | Met | Thr | Thr | Val | Thr |
| | 915 | | | | 920 | | | | 925 | | | | | |
| Gly | Thr | Asn | Gly | Val | Pro | Thr | Asp | Glu | Thr | Val | Ile | Val | Ile | Arg | Thr |
| | 930 | | | | 935 | | | | 940 | | | | | |
| Pro | Thr | Ser | Glu | Gly | Leu | Ile | Ser | Thr | Thr | Thr | Glu | Pro | Trp | Thr | Gly |
| 945 | | | | | 950 | | | | 955 | | | | | 960 |
| Thr | Phe | Thr | Ser | Thr | Ser | Thr | Glu | Val | Thr | Thr | Ile | Thr | Gly | Thr | Asn |
| | | | 965 | | | | 970 | | | | | 975 |
| Gly | Gln | Pro | Thr | Asp | Glu | Thr | Val | Ile | Val | Ile | Arg | Thr | Pro | Thr | Ser |
| | | | 980 | | | | 985 | | | | 990 | | |
| Glu | Gly | Leu | Ile | Ser | Thr | Thr | Thr | Glu | Pro | Trp | Thr | Gly | Thr | Phe | Thr |
| | | | 995 | | | | 1000 | | | | 1005 | | |
| Ser | Thr | Ser | Thr | Glu | Met | Thr | Thr | Val | Thr | Gly | Thr | Asn | Gly | Gln | Pro |
| | | 1010 | | | | 1015 | | | | 1020 | | |
| Thr | Asp | Glu | Thr | Val | Ile | Val | Ile | Arg | Thr | Pro | Thr | Ser | Glu | Gly | Leu |
| 1025 | | | | 1030 | | | | 1035 | | | | 1040 |
| Val | Thr | Thr | Thr | Thr | Glu | Pro | Trp | Thr | Gly | Thr | Phe | Thr | Ser | Thr | Ser |
| | | | | 1045 | | | | 1050 | | | | 1055 |
| Thr | Glu | Met | Ser | Thr | Val | Thr | Gly | Thr | Asn | Gly | Leu | Pro | Thr | Asp | Glu |
| | | | 1060 | | | | 1065 | | | | 1070 |
| Thr | Val | Ile | Val | Val | Lys | Thr | Pro | Thr | Thr | Ala | Ile | Ser | Ser | Ser | Leu |
| | | 1075 | | | | 1080 | | | | 1085 | | |
| Ser | Ser | Ser | Ser | Ser | Gly | Gln | Ile | Thr | Ser | Ser | Ile | Thr | Ser | Ser | Arg |
| | 1090 | | | | 1095 | | | | 1100 | | |
| Pro | Ile | Ile | Thr | Pro | Phe | Tyr | Pro | Ser | Asn | Gly | Thr | Ser | Val | Ile | Ser |
| 1105 | | | | 1110 | | | | 1115 | | | 1120 |
| Ser | Ser | Val | Ile | Ser | Ser | Ser | Val | Thr | Ser | Ser | Leu | Phe | Thr | Ser | Ser |
| | | | | 1125 | | | | 1130 | | | | 1135 |

```
Pro  Val  Ile  Ser  Ser  Ser  Val  Ile  Ser  Ser  Ser  Thr  Thr  Thr  Ser  Thr
               1140                 1145                    1150

Ser  Ile  Phe  Ser  Glu  Ser  Ser  Lys  Ser  Ser  Val  Ile  Pro  Thr  Ser  Ser
               1155                 1160                    1165

Ser  Thr  Ser  Gly  Ser  Ser  Glu  Ser  Glu  Thr  Ser  Ser  Ala  Gly  Ser  Val
     1170                 1175                    1180

Ser  Ser  Ser  Ser  Phe  Ile  Ser  Ser  Glu  Ser  Ser  Lys  Ser  Pro  Thr  Tyr
1185                 1190                 1195                         1200

Ser  Ser  Ser  Ser  Leu  Pro  Leu  Val  Thr  Ser  Ala  Thr  Thr  Ser  Gln  Glu
               1205                 1210                    1215

Thr  Ala  Ser  Ser  Leu  Pro  Pro  Ala  Thr  Thr  Lys  Thr  Ser  Glu  Gln
               1220                 1225                    1230

Thr  Thr  Leu  Val  Thr  Val  Thr  Ser  Cys  Glu  Ser  His  Val  Cys  Thr  Glu
               1235                 1240                    1245

Ser  Ile  Ser  Pro  Ala  Ile  Val  Ser  Thr  Ala  Thr  Val  Thr  Val  Ser  Gly
          1250                 1255                    1260

Val  Thr  Thr  Glu  Tyr  Thr  Thr  Trp  Cys  Pro  Ile  Ser  Thr  Thr  Glu  Thr
1265                 1270                 1275                         1280

Thr  Lys  Gln  Thr  Lys  Gly  Thr  Thr  Glu  Gln  Thr  Thr  Glu  Thr  Thr  Lys
               1285                 1290                    1295

Gln  Thr  Thr  Val  Val  Thr  Ile  Ser  Ser  Cys  Glu  Ser  Asp  Val  Cys  Ser
               1300                 1305                    1310

Lys  Thr  Ala  Ser  Pro  Ala  Ile  Val  Ser  Thr  Ser  Thr  Ala  Thr  Ile  Asn
               1315                 1320                    1325

Gly  Val  Thr  Thr  Glu  Tyr  Thr  Thr  Trp  Cys  Pro  Ile  Ser  Thr  Thr  Glu
     1330                 1335                    1340

Ser  Arg  Gln  Gln  Thr  Thr  Leu  Val  Thr  Val  Thr  Ser  Cys  Glu  Ser  Gly
1345                 1350                 1355                         1360

Val  Cys  Ser  Glu  Thr  Ala  Ser  Pro  Ala  Ile  Val  Ser  Thr  Ala  Thr  Ala
               1365                 1370                    1375

Thr  Val  Asn  Asp  Val  Val  Thr  Val  Tyr  Pro  Thr  Trp  Arg  Pro  Gln  Thr
               1380                 1385                    1390

Ala  Asn  Glu  Glu  Ser  Val  Ser  Ser  Lys  Met  Asn  Ser  Ala  Thr  Gly  Glu
               1395                 1400                    1405

Thr  Thr  Thr  Asn  Thr  Leu  Ala  Ala  Glu  Thr  Thr  Thr  Asn  Thr  Val  Ala
     1410                 1415                    1420

Ala  Glu  Thr  Ile  Thr  Asn  Thr  Gly  Ala  Ala  Glu  Thr  Lys  Thr  Val  Val
1425                 1430                 1435                         1440

Thr  Ser  Ser  Leu  Ser  Arg  Ser  Asn  His  Ala  Glu  Thr  Gln  Thr  Ala  Ser
               1445                 1450                    1455

Ala  Thr  Asp  Val  Ile  Gly  His  Ser  Ser  Val  Val  Ser  Val  Ser  Glu
               1460                 1465                    1470

Thr  Gly  Asn  Thr  Lys  Ser  Leu  Thr  Ser  Ser  Gly  Leu  Ser  Thr  Met  Ser
               1475                 1480                    1485

Gln  Gln  Pro  Arg  Ser  Thr  Pro  Ala  Ser  Ser  Met  Val  Gly  Tyr  Ser  Thr
               1490                 1495                    1500

Ala  Ser  Leu  Glu  Ile  Ser  Thr  Tyr  Ala  Gly  Ser  Ala  Asn  Ser  Leu  Leu
1505                 1510                 1515                         1520

Ala  Gly  Ser  Gly  Leu  Ser  Val  Phe  Ile  Ala  Ser  Leu  Leu  Leu  Ala  Ile
               1525                 1530                    1535

Ile
```

( 2 ) INFORMATION FOR SEQ ID NO:3:

( i ) SEQUENCE CHARACTERISTICS:
        ( A ) LENGTH: 2589 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Saccharomyces cerevisiae
        ( B ) STRAIN: ABXL-1D ( i x ) FEATURE:
        ( A ) NAME/KEY: CDS
        ( B ) LOCATION: 1..2589

( x i ) SEQUENCE DESCRIPTION: SEQ ID NO:3:

```
ATG ACA ATG CCT CAT CGC TAT ATG TTT TTG GCA GTC TTT ACA CTT CTG      48
Met Thr Met Pro His Arg Tyr Met Phe Leu Ala Val Phe Thr Leu Leu
 1               5                  10                  15

GCA CTA ACT AGT GTG GCC TCA GGA GCC ACA GAG GCG TGC TTA CCA GCA      96
Ala Leu Thr Ser Val Ala Ser Gly Ala Thr Glu Ala Cys Leu Pro Ala
             20                  25                  30

GGC CAG AGG AAA AGT GGG ATG AAT ATA AAT TTT TAC CAG TAT TCA TTG     144
Gly Gln Arg Lys Ser Gly Met Asn Ile Asn Phe Tyr Gln Tyr Ser Leu
         35                  40                  45

AAA GAT TCC TCC ACA TAT TCG AAT GCA GCA TAT ATG GCT TAT GGA TAT     192
Lys Asp Ser Ser Thr Tyr Ser Asn Ala Ala Tyr Met Ala Tyr Gly Tyr
     50                  55                  60

GCC TCA AAA ACC AAA CTA GGT TCT GTC GGA GGA CAA ACT GAT ATC TCG     240
Ala Ser Lys Thr Lys Leu Gly Ser Val Gly Gly Gln Thr Asp Ile Ser
 65                  70                  75                  80

ATT GAT TAT AAT ATT CCC TGT GTT AGT TCA TCA GGC ACA TTT CCT TGT     288
Ile Asp Tyr Asn Ile Pro Cys Val Ser Ser Ser Gly Thr Phe Pro Cys
                 85                  90                  95

CCT CAA GAA GAT TCC TAT GGA AAC TGG GGA TGC AAA GGA ATG GGT GCT     336
Pro Gln Glu Asp Ser Tyr Gly Asn Trp Gly Cys Lys Gly Met Gly Ala
            100                 105                 110

TGT TCT AAT AGT CAA GGA ATT GCA TAC TGG AGT ACT GAT TTA TTT GGT     384
Cys Ser Asn Ser Gln Gly Ile Ala Tyr Trp Ser Thr Asp Leu Phe Gly
        115                 120                 125

TTC TAT ACT ACC CCA ACA AAC GTA ACC CTA GAA ATG ACA GGT TAT TTT     432
Phe Tyr Thr Thr Pro Thr Asn Val Thr Leu Glu Met Thr Gly Tyr Phe
    130                 135                 140

TTA CCA CCA CAG ACG GGT TCT TAC ACA TTC AAG TTT GCT ACA GTT GAC     480
Leu Pro Pro Gln Thr Gly Ser Tyr Thr Phe Lys Phe Ala Thr Val Asp
145                 150                 155                 160

GAC TCT GCA ATT CTA TCA GTA GGT GGT GCA ACC GCG TTC AAC TGT TGT     528
Asp Ser Ala Ile Leu Ser Val Gly Gly Ala Thr Ala Phe Asn Cys Cys
                165                 170                 175

GCT CAA CAG CAA CCG CCG ATC ACA TCA ACG AAC TTT ACC ATT GAC GGT     576
Ala Gln Gln Gln Pro Pro Ile Thr Ser Thr Asn Phe Thr Ile Asp Gly
            180                 185                 190

ATC AAG CCA TGG GGT GGA AGT TTG CCA CCT AAT ATC GAA GGA ACC GTC     624
Ile Lys Pro Trp Gly Gly Ser Leu Pro Pro Asn Ile Glu Gly Thr Val
        195                 200                 205

TAT ATG TAC GCT GGC TAC TAT TAT CCA ATG AAG GTT GTT TAC TCG AAC     672
Tyr Met Tyr Ala Gly Tyr Tyr Tyr Pro Met Lys Val Val Tyr Ser Asn
    210                 215                 220

GCT GTT TCT TGG GGT ACA CTT CCA ATT AGT GTG ACA CTT CCA GAT GGT     720
Ala Val Ser Trp Gly Thr Leu Pro Ile Ser Val Thr Leu Pro Asp Gly
225                 230                 235                 240
```

| | | | | | | | | | | | | | | | | |
|---|---|---|---|---|---|---|---|---|---|---|---|---|---|---|---|---|
| ACC | ACT | GTA | AGT | GAT | GAC | TTC | GAA | GGG | TAC | GTC | TAT | TCC | TTT | GAC | GAT | 768 |
| Thr | Thr | Val | Ser | Asp | Asp | Phe | Glu | Gly | Tyr | Val | Tyr | Ser | Phe | Asp | Asp | |
| | | | 245 | | | | | 250 | | | | | | 255 | | |
| GAC | CTA | AGT | CAA | TCT | AAC | TGT | ACT | GTC | CCT | GAC | CCT | TCA | AAT | TAT | GCT | 816 |
| Asp | Leu | Ser | Gln | Ser | Asn | Cys | Thr | Val | Pro | Asp | Pro | Ser | Asn | Tyr | Ala | |
| | | | 260 | | | | 265 | | | | | 270 | | | | |
| GTC | AGT | ACC | ACT | ACA | ACT | ACA | ACG | GAA | CCA | TGG | ACC | GGT | ACT | TTC | ACT | 864 |
| Val | Ser | Thr | Thr | Thr | Thr | Thr | Thr | Glu | Pro | Trp | Thr | Gly | Thr | Phe | Thr | |
| | | 275 | | | | | 280 | | | | | 285 | | | | |
| TCT | ACA | TCT | ACT | GAA | ATG | ACC | ACC | GTC | ACC | GGT | ACC | AAC | GGC | GTT | CCA | 912 |
| Ser | Thr | Ser | Thr | Glu | Met | Thr | Thr | Val | Thr | Gly | Thr | Asn | Gly | Val | Pro | |
| | 290 | | | | | 295 | | | | | 300 | | | | | |
| ACT | GAC | GAA | ACC | GTC | ATT | GTC | ATC | AGA | ACT | CCA | ACA | ACT | GCT | AGC | ACC | 960 |
| Thr | Asp | Glu | Thr | Val | Ile | Val | Ile | Arg | Thr | Pro | Thr | Thr | Ala | Ser | Thr | |
| 305 | | | | 310 | | | | | 315 | | | | | | 320 | |
| ATC | ATA | ACT | ACA | ACT | GAG | CCA | TGG | ACT | GGT | ACT | TTC | ACT | TCT | ACA | TCT | 1008 |
| Ile | Ile | Thr | Thr | Thr | Glu | Pro | Trp | Thr | Gly | Thr | Phe | Thr | Ser | Thr | Ser | |
| | | | | 325 | | | | | 330 | | | | | 335 | | |
| ACT | GAA | ATG | ACC | ACC | GTC | ACC | GGT | ACT | AAC | GGT | CAA | CCA | ACT | GAC | GAA | 1056 |
| Thr | Glu | Met | Thr | Thr | Val | Thr | Gly | Thr | Asn | Gly | Gln | Pro | Thr | Asp | Glu | |
| | | | 340 | | | | | 345 | | | | | 350 | | | |
| ACC | GTG | ATT | GTT | ATC | AGA | ACT | CCA | ACC | AGT | GAA | GGT | TTG | GTT | ACA | ACC | 1104 |
| Thr | Val | Ile | Val | Ile | Arg | Thr | Pro | Thr | Ser | Glu | Gly | Leu | Val | Thr | Thr | |
| | | 355 | | | | | 360 | | | | | 365 | | | | |
| ACC | ACT | GAA | CCA | TGG | ACT | GGT | ACT | TTT | ACT | TCG | ACT | TCC | ACT | GAA | ATG | 1152 |
| Thr | Thr | Glu | Pro | Trp | Thr | Gly | Thr | Phe | Thr | Ser | Thr | Ser | Thr | Glu | Met | |
| | 370 | | | | | 375 | | | | | 380 | | | | | |
| TCT | ACT | GTC | ACT | GGA | ACC | AAT | GGC | TTG | CCA | ACT | GAT | GAA | ACT | GTC | ATT | 1200 |
| Ser | Thr | Val | Thr | Gly | Thr | Asn | Gly | Leu | Pro | Thr | Asp | Glu | Thr | Val | Ile | |
| 385 | | | | | 390 | | | | | 395 | | | | | 400 | |
| GTT | GTC | AAA | ACT | CCA | ACT | ACT | GCC | ATC | TCA | TCC | AGT | TTG | TCA | TCA | TCA | 1248 |
| Val | Val | Lys | Thr | Pro | Thr | Thr | Ala | Ile | Ser | Ser | Ser | Leu | Ser | Ser | Ser | |
| | | | | 405 | | | | 410 | | | | | 415 | | | |
| TCT | TCA | GGA | CAA | ATC | ACC | AGC | TCT | ATC | ACG | TCT | TCG | CGT | CCA | ATT | ATT | 1296 |
| Ser | Ser | Gly | Gln | Ile | Thr | Ser | Ser | Ile | Thr | Ser | Ser | Arg | Pro | Ile | Ile | |
| | | | 420 | | | | | 425 | | | | | 430 | | | |
| ACC | CCA | TTC | TAT | CCT | AGC | AAT | GGA | ACT | TCT | GTG | ATT | TCT | TCC | TCA | GTA | 1344 |
| Thr | Pro | Phe | Tyr | Pro | Ser | Asn | Gly | Thr | Ser | Val | Ile | Ser | Ser | Ser | Val | |
| | | 435 | | | | | 440 | | | | | 445 | | | | |
| ATT | TCT | TCC | TCA | GTC | ACT | TCT | TCT | CTA | TTC | ACT | TCT | TCT | CCA | GTC | ATT | 1392 |
| Ile | Ser | Ser | Ser | Val | Thr | Ser | Ser | Leu | Phe | Thr | Ser | Ser | Pro | Val | Ile | |
| | 450 | | | | | 455 | | | | | 460 | | | | | |
| TCT | TCC | TCA | GTC | ATT | TCT | TCT | TCT | ACA | ACA | ACC | TCC | ACT | TCT | ATA | TTT | 1440 |
| Ser | Ser | Ser | Val | Ile | Ser | Ser | Ser | Thr | Thr | Thr | Ser | Thr | Ser | Ile | Phe | |
| 465 | | | | | 470 | | | | | 475 | | | | | 480 | |
| TCT | GAA | TCA | TCT | AAA | TCA | TCC | GTC | ATT | CCA | ACC | AGT | AGT | TCC | ACC | TCT | 1488 |
| Ser | Glu | Ser | Ser | Lys | Ser | Ser | Val | Ile | Pro | Thr | Ser | Ser | Ser | Thr | Ser | |
| | | | | 485 | | | | | 490 | | | | | 495 | | |
| GGT | TCT | TCT | GAG | AGC | GAA | ACG | AGT | TCA | GCT | GGT | TCT | GTC | TCT | TCT | TCC | 1536 |
| Gly | Ser | Ser | Glu | Ser | Glu | Thr | Ser | Ser | Ala | Gly | Ser | Val | Ser | Ser | Ser | |
| | | | 500 | | | | | 505 | | | | | 510 | | | |
| TCT | TTT | ATC | TCT | TCT | GAA | TCA | TCA | AAA | TCT | CCT | ACA | TAT | TCT | TCT | TCA | 1584 |
| Ser | Phe | Ile | Ser | Ser | Glu | Ser | Ser | Lys | Ser | Pro | Thr | Tyr | Ser | Ser | Ser | |
| | | 515 | | | | | 520 | | | | | 525 | | | | |
| TCA | TTA | CCA | CTT | GTT | ACC | AGT | GCG | ACA | ACA | AGC | CAG | GAA | ACT | GCT | TCT | 1632 |
| Ser | Leu | Pro | Leu | Val | Thr | Ser | Ala | Thr | Thr | Ser | Gln | Glu | Thr | Ala | Ser | |
| | 530 | | | | | 535 | | | | | 540 | | | | | |
| TCA | TTA | CCA | CCT | GCT | ACC | ACT | ACA | AAA | ACG | AGC | GAA | CAA | ACC | ACT | TTG | 1680 |
| Ser | Leu | Pro | Pro | Ala | Thr | Thr | Thr | Lys | Thr | Ser | Glu | Gln | Thr | Thr | Leu | |
| 545 | | | | | 550 | | | | | 555 | | | | | 560 | |

| | | | | | | | | | | | | | | | | |
|---|---|---|---|---|---|---|---|---|---|---|---|---|---|---|---|---|
| GTT | ACC | GTG | ACA | TCC | TGC | GAG | TCT | CAT | GTG | TGC | ACT | GAA | TCC | ATC | TCC | 1728 |
| Val | Thr | Val | Thr | Ser | Cys | Glu | Ser | His | Val | Cys | Thr | Glu | Ser | Ile | Ser | |
| | | | | 565 | | | | | 570 | | | | | 575 | | |
| CCT | GCG | ATT | GTT | TCC | ACA | GCT | ACT | GTT | ACT | GTT | AGC | GGC | GTC | ACA | ACA | 1776 |
| Pro | Ala | Ile | Val | Ser | Thr | Ala | Thr | Val | Thr | Val | Ser | Gly | Val | Thr | Thr | |
| | | | 580 | | | | | 585 | | | | | 590 | | | |
| GAG | TAT | ACC | ACA | TGG | TGC | CCT | ATT | TCT | ACT | ACA | GAG | ACA | ACA | AAG | CAA | 1824 |
| Glu | Tyr | Thr | Thr | Trp | Cys | Pro | Ile | Ser | Thr | Thr | Glu | Thr | Thr | Lys | Gln | |
| | | 595 | | | | | 600 | | | | | 605 | | | | |
| ACC | AAA | GGG | ACA | ACA | GAG | CAA | ACC | ACA | GAA | ACA | ACA | AAA | CAA | ACC | ACG | 1872 |
| Thr | Lys | Gly | Thr | Thr | Glu | Gln | Thr | Thr | Glu | Thr | Thr | Lys | Gln | Thr | Thr | |
| | 610 | | | | | 615 | | | | | 620 | | | | | |
| GTA | GTT | ACA | ATT | TCT | TCT | TGT | GAA | TCT | GAC | GTA | TGC | TCT | AAG | ACT | GCT | 1920 |
| Val | Val | Thr | Ile | Ser | Ser | Cys | Glu | Ser | Asp | Val | Cys | Ser | Lys | Thr | Ala | |
| 625 | | | | | 630 | | | | | 635 | | | | | 640 | |
| TCT | CCA | GCC | ATT | GTA | TCT | ACA | AGC | ACT | GCT | ACT | ATT | AAC | GGC | GTT | ACT | 1968 |
| Ser | Pro | Ala | Ile | Val | Ser | Thr | Ser | Thr | Ala | Thr | Ile | Asn | Gly | Val | Thr | |
| | | | | 645 | | | | | 650 | | | | | 655 | | |
| ACA | GAA | TAC | ACA | ACA | TGG | TGT | CCT | ATT | TCC | ACC | ACA | GAA | TCG | AGG | CAA | 2016 |
| Thr | Glu | Tyr | Thr | Thr | Trp | Cys | Pro | Ile | Ser | Thr | Thr | Glu | Ser | Arg | Gln | |
| | | | 660 | | | | | 665 | | | | | 670 | | | |
| CAA | ACA | ACG | CTA | GTT | ACT | GTT | ACT | TCC | TGC | GAA | TCT | GGT | GTG | TGT | TCC | 2064 |
| Gln | Thr | Thr | Leu | Val | Thr | Val | Thr | Ser | Cys | Glu | Ser | Gly | Val | Cys | Ser | |
| | | 675 | | | | | 680 | | | | | 685 | | | | |
| GAA | ACT | GCT | TCA | CCT | GCC | ATT | GTT | TCG | ACG | GCC | ACG | GCT | ACT | GTG | AAT | 2112 |
| Glu | Thr | Ala | Ser | Pro | Ala | Ile | Val | Ser | Thr | Ala | Thr | Ala | Thr | Val | Asn | |
| | 690 | | | | | 695 | | | | | 700 | | | | | |
| GAT | GTT | GTT | ACG | GTC | TAT | CCT | ACA | TGG | AGG | CCA | CAG | ACT | GCG | AAT | GAA | 2160 |
| Asp | Val | Val | Thr | Val | Tyr | Pro | Thr | Trp | Arg | Pro | Gln | Thr | Ala | Asn | Glu | |
| 705 | | | | | 710 | | | | | 715 | | | | | 720 | |
| GAG | TCT | GTC | AGC | TCT | AAA | ATG | AAC | AGT | GCT | ACC | GGT | GAG | ACA | ACA | ACC | 2208 |
| Glu | Ser | Val | Ser | Ser | Lys | Met | Asn | Ser | Ala | Thr | Gly | Glu | Thr | Thr | Thr | |
| | | | | 725 | | | | | 730 | | | | | 735 | | |
| AAT | ACT | TTA | GCT | GCT | GAA | ACG | ACT | ACC | AAT | ACT | GTA | GCT | GCT | GAG | ACG | 2256 |
| Asn | Thr | Leu | Ala | Ala | Glu | Thr | Thr | Thr | Asn | Thr | Val | Ala | Ala | Glu | Thr | |
| | | | 740 | | | | | 745 | | | | | 750 | | | |
| ATT | ACC | AAT | ACT | GGA | GCT | GCT | GAG | ACG | AAA | ACA | GTA | GTC | ACC | TCT | TCG | 2304 |
| Ile | Thr | Asn | Thr | Gly | Ala | Ala | Glu | Thr | Lys | Thr | Val | Val | Thr | Ser | Ser | |
| | | 755 | | | | | 760 | | | | | 765 | | | | |
| CTT | TCA | AGA | TCT | AAT | CAC | GCT | GAA | ACA | CAG | ACG | GCT | TCC | GCG | ACC | GAT | 2352 |
| Leu | Ser | Arg | Ser | Asn | His | Ala | Glu | Thr | Gln | Thr | Ala | Ser | Ala | Thr | Asp | |
| | 770 | | | | | 775 | | | | | 780 | | | | | |
| GTG | ATT | GGT | CAC | AGC | AGT | AGT | GTT | GTT | TCT | GTA | TCC | GAA | ACT | GGC | AAC | 2400 |
| Val | Ile | Gly | His | Ser | Ser | Ser | Val | Val | Ser | Val | Ser | Glu | Thr | Gly | Asn | |
| 785 | | | | | 790 | | | | | 795 | | | | | 800 | |
| ACC | AAG | AGT | CTA | ACA | AGT | TCC | GGG | TTG | AGT | ACT | ATG | TCG | CAA | CAG | CCT | 2448 |
| Thr | Lys | Ser | Leu | Thr | Ser | Ser | Gly | Leu | Ser | Thr | Met | Ser | Gln | Gln | Pro | |
| | | | | 805 | | | | | 810 | | | | | 815 | | |
| CGT | AGC | ACA | CCA | GCA | AGC | AGC | ATG | GTA | GGA | TAT | AGT | ACA | GCT | TCT | TTA | 2496 |
| Arg | Ser | Thr | Pro | Ala | Ser | Ser | Met | Val | Gly | Tyr | Ser | Thr | Ala | Ser | Leu | |
| | | | 820 | | | | | 825 | | | | | 830 | | | |
| GAA | ATT | TCA | ACG | TAT | GCT | GGC | AGT | GCC | AAC | AGC | TTA | CTG | GCC | GGT | AGT | 2544 |
| Glu | Ile | Ser | Thr | Tyr | Ala | Gly | Ser | Ala | Asn | Ser | Leu | Leu | Ala | Gly | Ser | |
| | | 835 | | | | | 840 | | | | | 845 | | | | |
| GGT | TTA | AGT | GTC | TTC | ATT | GCG | TCC | TTA | TTG | CTG | GCA | ATT | ATT | TAA | | 2589 |
| Gly | Leu | Ser | Val | Phe | Ile | Ala | Ser | Leu | Leu | Leu | Ala | Ile | Ile | * | | |
| | 850 | | | | | 855 | | | | | 860 | | | | | |

( 2 ) INFORMATION FOR SEQ ID NO:4:

( i ) SEQUENCE CHARACTERISTICS:
        ( A ) LENGTH: 862 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Thr Met Pro His Arg Tyr Met Phe Leu Ala Val Phe Thr Leu Leu
 1               5                  10                  15
Ala Leu Thr Ser Val Ala Ser Gly Ala Thr Glu Ala Cys Leu Pro Ala
                20                  25                  30
Gly Gln Arg Lys Ser Gly Met Asn Ile Asn Phe Tyr Gln Tyr Ser Leu
            35                  40                  45
Lys Asp Ser Ser Thr Tyr Ser Asn Ala Ala Tyr Met Ala Tyr Gly Tyr
         50                  55                  60
Ala Ser Lys Thr Lys Leu Gly Ser Val Gly Gly Gln Thr Asp Ile Ser
 65                  70                  75                  80
Ile Asp Tyr Asn Ile Pro Cys Val Ser Ser Ser Gly Thr Phe Pro Cys
                 85                  90                  95
Pro Gln Glu Asp Ser Tyr Gly Asn Trp Gly Cys Lys Gly Met Gly Ala
                100                 105                 110
Cys Ser Asn Ser Gln Gly Ile Ala Tyr Trp Ser Thr Asp Leu Phe Gly
            115                 120                 125
Phe Tyr Thr Thr Pro Thr Asn Val Thr Leu Glu Met Thr Gly Tyr Phe
        130                 135                 140
Leu Pro Pro Gln Thr Gly Ser Tyr Thr Phe Lys Phe Ala Thr Val Asp
145                 150                 155                 160
Asp Ser Ala Ile Leu Ser Val Gly Gly Ala Thr Ala Phe Asn Cys Cys
                165                 170                 175
Ala Gln Gln Gln Pro Pro Ile Thr Ser Thr Asn Phe Thr Ile Asp Gly
            180                 185                 190
Ile Lys Pro Trp Gly Gly Ser Leu Pro Pro Asn Ile Glu Gly Thr Val
        195                 200                 205
Tyr Met Tyr Ala Gly Tyr Tyr Tyr Pro Met Lys Val Val Tyr Ser Asn
    210                 215                 220
Ala Val Ser Trp Gly Thr Leu Pro Ile Ser Val Thr Leu Pro Asp Gly
225                 230                 235                 240
Thr Thr Val Ser Asp Asp Phe Glu Gly Tyr Val Tyr Ser Phe Asp Asp
                245                 250                 255
Asp Leu Ser Gln Ser Asn Cys Thr Val Pro Asp Pro Ser Asn Tyr Ala
            260                 265                 270
Val Ser Thr Thr Thr Thr Thr Glu Pro Trp Thr Gly Thr Phe Thr
        275                 280                 285
Ser Thr Ser Thr Glu Met Thr Thr Val Thr Gly Thr Asn Gly Val Pro
    290                 295                 300
Thr Asp Glu Thr Val Ile Val Ile Arg Thr Pro Thr Thr Ala Ser Thr
305                 310                 315                 320
Ile Ile Thr Thr Thr Glu Pro Trp Thr Gly Thr Phe Thr Ser Thr Ser
                325                 330                 335
Thr Glu Met Thr Thr Val Thr Gly Thr Asn Gly Gln Pro Thr Asp Glu
            340                 345                 350
Thr Val Ile Val Ile Arg Thr Pro Thr Ser Glu Gly Leu Val Thr Thr
        355                 360                 365
```

| | | | | | | | | | | | | | | |
|---|---|---|---|---|---|---|---|---|---|---|---|---|---|---|
|Thr|Thr 370|Glu|Pro|Trp|Thr|Gly 375|Thr|Phe|Thr|Ser 380|Ser|Thr|Glu|Met|
|Ser 385|Thr|Val|Thr|Gly|Thr 390|Asn|Gly|Leu|Pro|Thr 395|Asp|Glu|Thr|Val|Ile 400|
|Val|Val|Lys|Thr|Pro 405|Thr|Thr|Ala|Ile|Ser 410|Ser|Ser|Leu|Ser|Ser 415|Ser|
|Ser|Ser|Gly|Gln 420|Ile|Thr|Ser|Ser|Ile 425|Thr|Ser|Ser|Arg|Pro 430|Ile|Ile|
|Thr|Pro|Phe 435|Tyr|Pro|Ser|Asn|Gly 440|Thr|Ser|Val|Ile|Ser 445|Ser|Ser|Val|
|Ile|Ser 450|Ser|Ser|Val|Thr|Ser 455|Ser|Leu|Phe|Thr|Ser 460|Ser|Pro|Val|Ile|
|Ser 465|Ser|Ser|Val|Ile|Ser 470|Ser|Ser|Thr|Thr|Thr 475|Ser|Thr|Ser|Ile|Phe 480|
|Ser|Glu|Ser|Ser|Lys 485|Ser|Ser|Val|Ile|Pro 490|Thr|Ser|Ser|Ser|Thr 495|Ser|
|Gly|Ser|Ser|Glu 500|Ser|Glu|Thr|Ser|Ser 505|Ala|Gly|Ser|Val|Ser 510|Ser|Ser|
|Ser|Phe|Ile 515|Ser|Ser|Glu|Ser|Ser 520|Lys|Ser|Pro|Thr|Tyr 525|Ser|Ser|Ser|
|Ser|Leu 530|Pro|Leu|Val|Thr|Ser 535|Ala|Thr|Thr|Ser|Gln 540|Glu|Thr|Ala|Ser|
|Ser 545|Leu|Pro|Pro|Ala|Thr 550|Thr|Thr|Lys|Thr|Ser 555|Glu|Gln|Thr|Thr|Leu 560|
|Val|Thr|Val|Thr|Ser 565|Cys|Glu|Ser|His|Val 570|Cys|Thr|Glu|Ser|Ile 575|Ser|
|Pro|Ala|Ile|Val 580|Ser|Thr|Ala|Thr|Val 585|Thr|Val|Ser|Gly|Val 590|Thr|Thr|
|Glu|Tyr|Thr 595|Thr|Trp|Cys|Pro|Ile 600|Ser|Thr|Thr|Glu|Thr 605|Thr|Lys|Gln|
|Thr|Lys 610|Gly|Thr|Thr|Glu|Gln 615|Thr|Thr|Glu|Thr|Thr 620|Lys|Gln|Thr|Thr|
|Val 625|Val|Thr|Ile|Ser|Ser 630|Cys|Glu|Ser|Asp|Val 635|Cys|Ser|Lys|Thr|Ala 640|
|Ser|Pro|Ala|Ile|Val 645|Ser|Thr|Ser|Thr|Ala 650|Thr|Ile|Asn|Gly|Val|Thr 655|
|Thr|Glu|Tyr|Thr 660|Thr|Trp|Cys|Pro|Ile 665|Ser|Thr|Thr|Glu|Ser 670|Arg|Gln|
|Gln|Thr|Thr 675|Leu|Val|Thr|Val|Thr 680|Ser|Cys|Glu|Ser|Gly 685|Val|Cys|Ser|
|Glu|Thr 690|Ala|Ser|Pro|Ala|Ile 695|Val|Ser|Thr|Ala|Thr 700|Ala|Thr|Val|Asn|
|Asp 705|Val|Val|Thr|Val|Tyr 710|Pro|Thr|Trp|Arg|Pro 715|Gln|Thr|Ala|Asn|Glu 720|
|Glu|Ser|Val|Ser|Ser 725|Lys|Met|Asn|Ser|Ala 730|Thr|Gly|Glu|Thr|Thr 735|Thr|
|Asn|Thr|Leu|Ala 740|Ala|Glu|Thr|Thr|Thr 745|Asn|Thr|Val|Ala|Ala 750|Glu|Thr|
|Ile|Thr|Asn 755|Thr|Gly|Ala|Ala|Glu 760|Thr|Lys|Thr|Val|Val 765|Thr|Ser|Ser|
|Leu|Ser 770|Arg|Ser|Asn|His|Ala 775|Glu|Thr|Gln|Thr|Ala 780|Ser|Ala|Thr|Asp|
|Val 785|Ile|Gly|His|Ser|Ser 790|Ser|Val|Val|Ser|Val 795|Ser|Glu|Thr|Gly|Asn 800|

Thr Lys Ser Leu Thr Ser Ser Gly Leu Ser Thr Met Ser Gln Gln Pro
              805                 810                 815

Arg Ser Thr Pro Ala Ser Ser Met Val Gly Tyr Ser Thr Ala Ser Leu
              820             825                 830

Glu Ile Ser Thr Tyr Ala Gly Ser Ala Asn Ser Leu Leu Ala Gly Ser
            835             840                 845

Gly Leu Ser Val Phe Ile Ala Ser Leu Leu Leu Ala Ile Ile
        850                 855             860

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:5:

CCCAAGCTTA AAAATGACAA TGCCTCATCG CTA                            33

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:6:

CCCAAGCTTT TAAATAATTG CCAGCAATAA GGA                            33

(2) INFORMATION FOR SEQ ID NO:7:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "Asn, Thr, Asp"

(ix) FEATURE:
        (A) NAME/KEY: Modified-site
        (B) LOCATION: 8
        (D) OTHER INFORMATION: /product= "Gly, Asp, Ser"

(ix) FEATURE:
        (A) NAME/KEY: Modified-site
        (B) LOCATION: 15
        (D) OTHER INFORMATION: /product= "Thr, Ala"

(ix) FEATURE:
        (A) NAME/KEY: Modified-site
        (B) LOCATION: 17
        (D) OTHER INFORMATION: /product= "Met, Leu, Val"

(ix) FEATURE:
        (A) NAME/KEY: Modified-site
        (B) LOCATION: 18
        (D) OTHER INFORMATION: /product= "Thr, Ser"

( i x ) FEATURE:
    ( A ) NAME/KEY: Modified-site
    ( B ) LOCATION: 20
    ( D ) OTHER INFORMATION: /product= "Val, Ile"

( i x ) FEATURE:
    ( A ) NAME/KEY: Modified-site
    ( B ) LOCATION: 26
    ( D ) OTHER INFORMATION: /product= "Leu, Val, Gln"

( i x ) FEATURE:
    ( A ) NAME/KEY: Modified-site
    ( B ) LOCATION: 27
    ( D ) OTHER INFORMATION: /product= "Pro, Arg"

( i x ) FEATURE:
    ( A ) NAME/KEY: Modified-site
    ( B ) LOCATION: 32
    ( D ) OTHER INFORMATION: /product= "Val, Ile"

( i x ) FEATURE:
    ( A ) NAME/KEY: Modified-site
    ( B ) LOCATION: 35
    ( D ) OTHER INFORMATION: /product= "Ile, Val"

( i x ) FEATURE:
    ( A ) NAME/KEY: Modified-site
    ( B ) LOCATION: 36
    ( D ) OTHER INFORMATION: /product= "Arg, Lys"

( i x ) FEATURE:
    ( A ) NAME/KEY: Modified-site
    ( B ) LOCATION: 40
    ( D ) OTHER INFORMATION: /product= "Thr, Ser"

( i x ) FEATURE:
    ( A ) NAME/KEY: Modified-site
    ( B ) LOCATION: 41
    ( D ) OTHER INFORMATION: /product= "Ala, Glu"

( i x ) FEATURE:
    ( A ) NAME/KEY: Modified-site
    ( B ) LOCATION: 42
    ( D ) OTHER INFORMATION: /product= "Thr, Gly, Ser, Ile"

( i x ) FEATURE:
    ( A ) NAME/KEY: Modified-site
    ( B ) LOCATION: 43
    ( D ) OTHER INFORMATION: /product= "Thr, Leu, Ser"

( i x ) FEATURE:
    ( A ) NAME/KEY: Modified-site
    ( B ) LOCATION: 44
    ( D ) OTHER INFORMATION: /product= "Ala, Ile, Val, Ser"

( i x ) FEATURE:
    ( A ) NAME/KEY: Modified-site
    ( B ) LOCATION: 45
    ( D ) OTHER INFORMATION: /product= "Met, Ser, Ile, Thr"

( x i ) SEQUENCE DESCRIPTION: SEQ ID NO:7:

```
Thr Thr Thr Glx Pro Trp Xaa Xaa Thr Phe Thr Ser Thr Ser Xaa Glu
1               5                   10                  15

Xaa Xaa Thr Xaa Thr Gly Thr Asn Gly Xaa Xaa Thr Asp Glu Thr Xaa
            20                  25                  30

Ile Val Xaa Xaa Thr Pro Thr Xaa Xaa Xaa Xaa Xaa Xaa
            35              40                  45
```